US006335409B1

(12) United States Patent
Herr et al.

(10) Patent No.: US 6,335,409 B1
(45) Date of Patent: Jan. 1, 2002

(54) CROSS-LINKABLE PHOTOACTIVE POLYMER MATERIALS

(75) Inventors: Rolf-Peter Herr, Lörrach (DE); François Herzog, Richwiller (FR); Andreas Schuster, Freiburg (DE)

(73) Assignee: Rolic AG, Basel (CH)

( * ) Notice: Subject to any disclaimer, the term of this patent is extended or adjusted under 35 U.S.C. 154(b) by 0 days.

(21) Appl. No.: 09/614,185

(22) Filed: Jul. 11, 2000

Related U.S. Application Data

(62) Division of application No. 08/708,333, filed on Sep. 4, 1996, now Pat. No. 6,107,427.

(30) Foreign Application Priority Data

Sep. 15, 1995 (CH) ............................................. 2615/95
Mar. 13, 1996 (CH) ............................................. 664/96

(51) Int. Cl.[7] ................................................ C08F 22/10
(52) U.S. Cl. ...................... 526/321; 526/319; 526/320; 526/326; 526/328
(58) Field of Search ................................ 526/321, 320, 526/319, 326

(56) References Cited

U.S. PATENT DOCUMENTS

| 4,974,941 A | 12/1990 | Gibbons et al. |
| 5,252,695 A | 10/1993 | Nicin |
| 5,539,074 A | 7/1996 | Herr et al. |

FOREIGN PATENT DOCUMENTS

| DE | 4408170 A1 | 9/1995 |
| EP | 0322708 | 7/1989 |
| EP | 0611786 A1 | 8/1994 |
| FR | 2609993 | 7/1988 |
| WO | WO 94/00797 | 1/1994 |

OTHER PUBLICATIONS

Namariyama et al. Kobunshi Ronbunshu, 35 (3), 145–50 (1978.
M Jean Farrall, Polymer Bulletin 11, pp. 191–194 (1984).
J.M. Guglielminetti et al., Polymer Bulletin 16, pp. 411–418 (1986).
P. Keller, Chemistry of Materials 2, pp. 3–4 (1990).
T. Koch et al., Macromol. Chem, 100, pp. 1369–1377 (1989).
R. Sinsemsuksakul et al., Journal of Molecular Structure, 348, pp. 175–178 (1995).
M.J. Whitcombe et al., Polymer, 34, pp. 1347–1353 (1993).
M.J. Whitcombe et al., Journal of Polymer Science Part A: Polymer Chemistry, 29, pp. 251–259 (1991).
M.J. Whitcombe et al, Jounal of Polymer Science Part A: Polymer Chemistry, 30, pp. 1681–1691 (1992).
K. Sugiyama et al., Kinkidaigaku Kogakubu Kenkyu Kokoku, 22, pp. 37–45 (1988).
Japanese Journal of Applied Physics 31: 2155–2164 (1992), Part 1, No. 7.

*Primary Examiner*—Fred Zitomer
(74) *Attorney, Agent, or Firm*—Finnegan, Henderson, Farabow, Garrett & Dunner, L.L.P.

(57) ABSTRACT

The invention is concerned with novel cross-linkable, photoactive polymer materials with 3-aryl-acrylic acid esters and amides as well as their use as orienting layers for liquid crystals and for the production of non-structured or structured optical elements and multi-layer systems.

22 Claims, No Drawings

CROSS-LINKABLE PHOTOACTIVE POLYMER MATERIALS

This is a division of application Ser. No. 08/708,333, filed Sep. 4, 1996, U.S. Pat. No. 6,107,427, which is incorporated herein by reference.

BACKGROUND OF THE INVENTION

1. Field

The present invention is concerned with novel cross-linkable, photoactive polymer materials having 3-arylacrylic acid esters and amides. The present invention also provides for the use of such materials as orienting layers for liquid crystals and for the production of non-structured and structured optical elements, and multi-layer systems.

2. Description

The orienting layer is of special significance in (electrooptical) liquid crystal indicators. It serves to guarantee a symmetrical and disturbance-free direct orientation of the molecular axis.

Uniaxially-rubbed polymer orienting layers such as polyamide are usually used for orienting liquid crystal molecules in liquid crystal indicators ("LCD's"). In this procedure, the direction of rubbing provides the direction of orientation. However, a number of serious disadvantages which can severely influence the optical quality of liquid crystal indicators, are associated with rubbing. For example, dust produced by rubbing can lead to optically defective sites in the display. At the same time, the polymer layer becomes electrostatically charged. In the case of thin film transistor ("TFT")-TN-LCD's, such eletrostatic charging can result in damage to the thin layer transistors which lie below it. For these reasons, the yield of optically perfect displays in LCD production has hitherto not been optimal.

A further disadvantage of rubbing is that it is not possible to produce structured orienting layers in a simple manner, since orientation direction cannot be locally varied by rubbing. Thus, only essentially uniformly directed layers of large area can be produced by rubbing. Structured orienting layers are, however, of great interest in many fields of display technology and integrated optics. For example, the viewing angle dependence of twisted nematic ("TN")-LCD's can be produced with such orienting layers.

Orienting layers in which the direction of orientation can be provided by irradiation with polarized light have been known for some time. Thus, problems inherent in rubbing can be avoided. In addition, the possibility exists of providing local variations of the direction of orientation and thus of structuring the orienting layer.

One possibility for the structured orientation of liquid crystals utilizes the ability of certain dye molecules to isomerize in order to induce a differential direction photochemically by irradiation with polarized light of suitable wavelength. This is achieved, for example, by admixing an orienting polymer and a dye, which is then irradiated with polarized light. Such a guest/host system is described, for example, in U.S. Pat. No. 4,974,941, the contents of which are herein incorporated by reference. In this system azobenzenes are incorporated in polyimide orienting layers and are subsequently irradiated with polarized light. Liquid crystals which are in contact with the surface of a thus-exposed layer are oriented correspondingly to this preferential direction. This orienting procedure is reversible, that is, the already inscribed direction of orientation can be reversed by repeating the irradiation of the layer with light of a second direction of polarization. Since this re-orientation procedure can be repeated at will, orienting layers on this basis are not very suitable for use in LCD's.

A further possibility for the production of high resolution orienting patterns in liquid crystalline layers is described in Jpn. J. Appl. Phys., 31:2155 (1992). In this procedure, dimerization of polymer-bound photoreactive cinnamic acid groups induced by irradiation with linear polarized light is utilized for the structured orientation of liquid crystals. In contrast to the reversible orientation procedure described above, an anisotropic polymer network is built up in the case of the photo-structurable orienting layers described in Jpn. J. Appl. Phys., 31:2155 (1992). These photo-orientated polymer networks are of use primarily where structured or non-structured liquid crystal orienting layers a re required. Moreover, such orienting layers can also be used in LCD's, for example, for the production of so-called hybrid layers as are exemplified in European Patent Applications 0 611 981, 0 689 084 and 0 689 065, and in Swiss Patent Application No. 2036/95 which correspond to U.S. application No. 08/194,234, U.S. Pat. No. 5,602,661 U.S. application No. 08/489,865, abandoned 08/489,866 abandoned and U.S. application No. 08/667,687, respectively, the contents of each being herein incorporated by reference. Optical elements such as non-absorptive color filters, linear and circular polarizers, optical retardation layers, etc. can be realized with these hybrid layers from photo-structured orienting polymers and cross-linkable low molecular liquid crystals.

Cinnamic acid polymers which are suitable in principal for the production of such an isotropic cross-linked, photo-structured orienting layers for liquid crystals are described, for example, in European Publication No. 0 611 786, corresponding to U.S. Pat. No. 5,539,074, the contents of which is herein incorporated by reference. These cross-linkable cinnamic acid derivatives are in principle linked to the main chain of the polymer via the carboxyl function of the cinnamic acid (phenylacrylic acid) and a spacer. In these polymers the dimerizable acrylic ester group of the cinnamic acid is always directed from "within" to the spacer and, respectively, polymer backbone, while the aromatic residue is always orientated "outwards" from the polymer backbone.

It has now been found that this method for directing the cinnamic acid in the known photopolymers is by no means optimal. Concurrent photochemical reactions have a damaging effect on the orientation capability. The known cinnamic acid polymers are distinguished by an insufficient photochemical long-term stability. For example, lengthy irradiation with UV light of a pre-finished orienting layer leads to damage of the originally present orientation. Multiple exposures in which the already existing orienting layer having a pre-given inscribed pattern is exposed once more in order to orientate still unexposed regions in a different direction can only be carried out when the previously exposed sites are covered by a mask. Otherwise, the already orientated regions of the layer can completely or partially lose their structure by photochemical side-reactions.

A further disadvantage of a previously used cinnamic acid polymers is that no viewing angle occurs in the case of the orienting surfaces from these materials produced by simple exposure to polarized light. However, especially for use in LCD's, the orienting layer must provide not only the direction of orientation, but also a viewing angle.

In the case of the aforementioned uniaxially rubbed polymer orienting layers this viewing angle is already produced by the rubbing procedure on the polymer surface. When a liquid crystal is brought into contact with such a surface, then the liquid crystal molecules lie inclined rather than parallel to the surface, which thus confers the viewing angle to the liquid crystal. The extent of the viewing angle is thus determined not only by rubbing parameter such as traversing velocity and contact pressure, but also by the chemical structure of the polymer. Viewing angles between 1° and 15° are required for the production of liquid crystal indicators depending on type. The greater viewing angles are required especially for supertwisted nematic ("STN") LCD's in order to avoid the appearance of so-called finger print textures. The rotational direction and the viewing direction in TN and TFT-TN-LCD's are determined by the viewing angle, whereby "reverse twist" and "reverse tilt" phenomena are prevented. While reverse twist in the switched-off state leads to regions having a false direction of rotation which is noticeable optically in a speckled appearance of the indicator, reverse tilt is noticeable with much optical disturbance primarily upon switching the LCD's by angling of the liquid crystals in different directions. Reverse twist can be prevented by doping the liquid crystal mixture with a chiral dopant having a suitable direction of rotation. However, for the suppression of reverse tilt there has hitherto been no alternative possibility to the use of orienting layers having a viewing angle.

SUMMARY OF THE INVENTION

The object of the invention is therefore to produce photoreactive polymers which do not have the disadvantages described above of the previously used cinnamic acid polymers, that is, the missing photochemical storage stability and primarily the missing viewing angle after irradiation with polarized light, and which are thus capable of producing stable high-resolution orienting patterns.

The subject invention provides a polymer composition which comprises units of the compound:

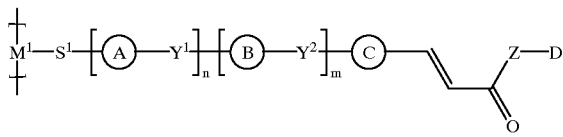

I wherein
- $M^1$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene derivative, and siloxane;
- $S^1$ is a spacer unit;
- ring A is unsubstituted phenylene, phenylene which is substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl, or piperazine-1,4-diyl;
- ring B is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl;
- $Y^1$, $Y^2$ each independently is a single covalent bond, —(CH$_2$)$_t$—, —O—, —CO—, —CO—O—, —O—OC—, —NR$^4$—, —CO—NR$^4$—, —R$^4$N—CO—, —(CH$_2$)$_u$—O—, —O—(CH$_2$)$_u$—, —(CH$_2$)$_u$—NR$^4$—, or —NR$^4$—(CH$_2$)$_u$—, in which
- $R^4$ is hydrogen or lower alkyl;
- t is a whole number from 1 to 4;
- u is a whole number from 1 to 3;
- m, n each independently is 0 or 1;
- ring C is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthlene, or 2,6-naphthylene;
- Z is —O— or —NR$^5$—, in which R$^5$ is hydrogen or lower alkyl, or a second group of formula D, in which
- D is an unsubstituted C$_1$–C$_{20}$ straight-chain alkyl group, an unsubstituted C$_1$–C$_{20}$ branched-chain alkyl group, a C$_1$–C$_{20}$ straight-chain alkyl group substituted with fluorine or chlorine, a branched-chain C$_1$–C$_{20}$ alkyl group substituted with fluorine or chlorine, an unsubstituted cycloalkyl residue with 3 to 8 ring atoms, or a cycloalkyl residue 3 to 8 ring atoms substituted with fluorine, chlorine, alkyl or alkoxy.

DETAILED DESCRIPTION OF THE INVENTION

The present invention will now be described in terms of its preferred embodiments. These embodiments are set forth to aid in understanding the subject invention, but are not to be construed as limiting.

It has surprisingly been found that side-chain polymers with 3-aryl-acrylic acid derivatives as the photoreactive unit, which are not bonded to the spacer and, respectively, the main chain of the polymer, not as the previously known cinnamic acid polymers "inwards" via the carboxyl function but via the aromatic residue and their photoreactive acrylate units are thus oriented "outwards" from the polymer backbone, fulfill these conditions and are outstandingly suitable as orienting layers for liquid crystals. In addition to a significantly higher photochemical stability of the orienting layer and a viewing angle, in the case of the polymers in accordance with the invention a substantially better orientation of the liquid crystal is achieved, which leads, for example, to a clearly improved contrast.

The object of the present invention are polymer compositions in which repeating units of formula I are present:

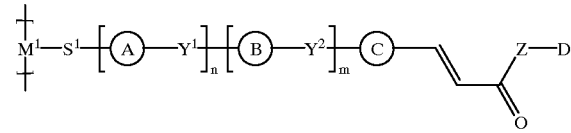

I wherein
- $M^1$ signifies a repeating monomer unit from the group; acrylate, methacrylate, 2-chloroacrylate, 2-phenylacrylate; optionally N-lower alkyl substituted acrylamide, methacrylamide, 2-chloroacrylamide and 2-phenylacrylamide; vinyl ether, vinyl ester, styrene derivative, siloxane;
- $S^1$ signifies spacer units such as, for example, a single covalent bond, a straight-chain or branched alkylene grouping represented hereinafter by —(CH$_2$)$_r$—, as well as —(CH$_2$)$_r$—O—, —(CH$_2$)$_r$—O—(CH$_2$)$_s$—, —(CH$_2$)$_r$—O—(CH$_2$)$_s$—O—, —(CH$_2$)$_r$—CO—, —(CH$_2$)$_r$—CO—O—, —(CH$_2$)$_r$—O—CO—, —(CH$_2$)$_r$—NR$^2$—, —(CH$_2$)$_r$—CO—NR$^2$—, —(CH$_2$)$_r$—NR$^2$—CO—, —(CH$_2$)$_r$—NR$^2$—CO—O— or —(CH$_2$)$_r$—NR$^2$—CO—NR$_3$—, which is optionally mono- or multiply-substituted with fluorine, chlorine or cyano and in which r and s are each a whole number of 1 to 20, with the proviso that r+s 20, and R$^2$ and R$^3$ each independently signify hydrogen or lower alkyl;

ring A signifies phenylene which is unsubstituted or optionally substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl, piperazine-1,4-diyl;

ring B signifies phenylene which is unsubstituted or optionally substituted with fluorine, chlorine, cyano, alkyl or alkoxy, pyridine-2,5-diyl, pyrimidine-2,5-diyl, 1,4- or 2,6-naphthylene, 1,3-dioxane-2,5-diyl, cyclohexane-1,4-diyl;

Y$^1$, Y$^2$ each independently signify a single covalent bond, —(CH$_2$)$_t$—, —O—, —CO—, —CO—O—, —O—OC—, —NR$^4$—, —CO—NR$^4$—, —R$^4$N—CO—, —(CH$_2$)$_u$—O—, —O—(CH$_2$)$_u$—, —(CH$_2$)$_u$—NR$^4$— or —NR$^4$—(CH$_2$)$_u$—, in which R$^4$ signifies hydrogen or lower alkyl;

t signifies a whole number of 1 to 4;

u signifies a whole number of 1 to 3;

m, n each independently signify 0 or 1;

ring C signifies phenylene which is unsubstituted or optionally substituted with fluorine, chlorine, cyano, alkyl or alkoxy, or pyrimidine-2,5-diyl, pyridine-2,5-diyl, 2,5-thiophenylene, 2,5-furanylene, 1,4- or 2,6-naphthylene;

Z signifies —O— or —NR$^5$—, in which R$^5$ signifies hydrogen or lower alkyl, or a second group of formula D, in which D signifies a straight-chain or branched alkyl group with 1 to 20 carbon atoms which is optionally substituted with fluorine or chlorine, a cycloalkyl residue with 3 to 8 ring atoms which is optionally substituted with fluorine, chlorine alkyl or alkoxy.

The use of the polymers in accordance with the invention as orienting layers for liquid crystals as well as their use in optical components, especially for the production of hybrid layer elements, are also objects of the present invention.

The polymer materials in accordance with the invention can be synthesized only from repeating units of general formula I (homopolymers) or they can contain further repeating units in addition to the repeating units of general formula I (copolymers). Preferred are copolymers with different repeating units. Homopolymers which contain structural units of formula I are especially preferred. The polymers in accordance with the invention have a molecular weight MW between 1,000 and 5,000,000, preferably however between 5,000 and 2,000,000, especially advantageously however between 10,000 and 1,000,000.

Comonomer units for the polymer materials in accordance with the invention with C—C linkages in the main chain can be further structures of formula I and/or however also other structures which are usual in polymer chemistry, such as, for example, straight-chain or branched alkyl esters of acrylic or methacrylic acid, allyl esters of acrylic or methacrylic acid, alkyl vinyl ethers or esters, phenoxyalkyl acrylates or phenoxyalkyl methacrylates, phenylalkyl acrylates or phenyla-lkyl methacrylates, hydroxyalkyl acrylates or hydroxyalkyl methacrylates with alkyl residues of 1 to 20, preferably 1 to 10, especially however with 1 to 6, carbon atoms, acrylonitrile, methacrylonitrile, styrene, 4-methylstyrene, and the like. Preferred comonomer units are structures of formula I, alkyl esters of acrylic or methacrylic acid, hydroxyalkyl acrylate, hydroxyalkyl methacrylate, acrylonitrile, methacrylonitrile or styrene, but especially structures of formula I, alkyl esters of acrylic or methacrylic acid, hydroxyalkyl acrylate or hydroxyalkyl methacrylate.

Comonomer units for siloxanes are preferably further siloxane structures of formula I and/or dimethyl siloxane groups.

The content of comonomer units in the polymers in accordance with the invention, which do not correspond to a structure of formula I, is smaller than or equal to 50%, preferably smaller than or equal to 30%, but especially smaller than or equal to 15%.

Under the term "copolymers" there are to be understood preferably statistical copolymers such as, for example, copolymers from different derivatives of formula I or from structures of formula I with acrylic acid, methacrylic acid or styrene derivatives. Homopolymers embrace linear and cyclic polymers such as, for example, cyclic polysiloxanes, but preferably linear polymers.

Repeating monomer units (M$^1$) are acrylates such as

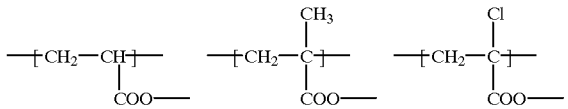

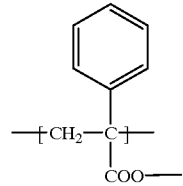

acrylamides such as

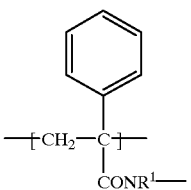

vinyl ether and vinyl ester such as

styrene derivatives such as

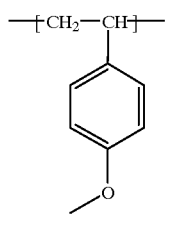 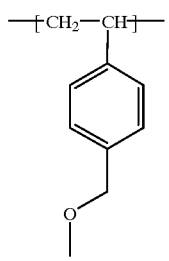

siloxanes such as

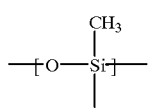

wherein $R^1$ signifies hydrogen or lower alkyl;

Preferred "monomer units" $M^1$ are acrylate, methacrylate, 2-chloroacrylate, acrylamide, methacrylamide, 2-chloroacrylamide, styrene derivatives and siloxanes. Acrylate, methacrylate, styrene derivatives and siloxanes are particularly preferred "monomer units" $M^1$. Quite especially preferred "monomer units" $M^1$ are acrylate, methacrylate and styrene derivatives.

The term "lower alkyl" taken alone or in combinations such as "lower alkoxy", "hydroxy-lower alkyl", "phenoxy-lower alkyl" "phenyl-lower alkyl", denotes, hereinbefore and hereinafter, straight-chain or branched saturated hydrocarbon residues with 1 to 6, preferably with 1 to 3, carbon atoms, such as methyl, ethyl, propyl, or i-propyl.

The term "alkyl" taken alone or in combinations such as "alkoxy", denotes, hereinbefore and hereinafter, straight-chain or branched saturated hydrocarbon residues with a maximum of 20 carbon atoms.

Preferred "spacer units" in the scope of the present invention include a single covalent bond, a straight-chain or branched alkylene grouping represented by —$(CH_2)_r$—, wherein r is a whole number of 1 to 8, especially 1 to 6, as well as —$(CH_2)_r$—O—, —$(CH_2)_r$—CO—O—, —$(CH_2)_r$—O—CO—, —$(CH_2)_r$—$NR^2$—, —$(CH_2)_r$—CO—$NR^2$— or —$(CH_2)_r$—$NR^2$—CO—, wherein $R^2$ signifies hydrogen or lower alkyl. The choice of "spacer units" is readily determinable to the skilled artisan.

Examples of preferred "spacer units" are the single bond, methylene, 1,2-ethylene, 1,3-propylene, 1,4-butylene, 1,5-pentylene, 1,6-hexylene, 1,7-heptylene, 1,8-octylene, 1,2-propylene, 2-methyl-1,2-propylene, 1,3-butylene, ethyleneoxy, ethyleneoxycarbonyl, ethyleneoyloxy, propyleneoxy, propyleneoxycarbonyl, propyleneoyloxy, butyleneoxy, butyleneoxycarbonyl, butyleneoyloxy, pentyleneoxy, pentyleneoxycarbonyl, pentyleneoyloxy, hexyleneoxy, hexyleneoxycarbonyl, hexyleneoyloxy, heptyleneoxy, heptyleneoxycarbonyl, heptyleneoyloxy, octyleneoxy, octyleneoxycarbonyl, octyleneoyloxy, ethyleneamino, propyleneamino, butyleneamino, pentyleneamino, hexyleneamino, heptyleneamino, octyleneamino, ethyleneaminocarbonyl, propyleneaminocarbonyl, butyleneaminocarbonyl, pentyleneaminocarbonyl, hexyleneaminocarbonyl, heptyleneaminocarbonyl, octyleneaminocarbonyl, ethylenecarbonylamino, propylenecarbonylamino, butylenecarbonylamino, pentylenecarbonylamino, hexylenecarbonylamino, heptylenecarbonylamino, octylenecarbonylamino, and the like.

Especially preferred "spacer units" are a single covalent bond, a straight-chain alkylene grouping represented by —$(CH_2)_r$—, wherein r is a whole number of 1 to 6, as well as —$(CH_2)_r$—O—, —$(CH_2)_r$—CO—O— and —$(CH_2)_r$—O—CO—.

Examples of especially preferred "spacer units" are the single bond, methylene, 1,2-ethylene, 1,3-propylene, 1,4-butylene, 1,5-pentylene, 1,6-hexylene, ethyleneoxy, ethyleneoxycarbonyl, ethyleneoyloxy, proyleneoxy, propyleneoxycarbonyl, propyleneoyloxy, butyleneoxy, butyleneoxycarbonyl, butyleneoyloxy, pentyleneoxy, pentyleneoxycarbonyl, pentyleneoyloxy, hexyleneoxy, hexyleneoxycarbonyl and hexyleneoyloxy.

The term "phenylene which is unsubstituted or optionally substituted with fluorine, chlorine, cyano, alkyl or alkoxy" embraces in the scope of the present invention 1,2-, 1,3- or 1,4-phenylene, especially however 1,3- or 1,4-phenylene, which is unsubstituted or mono- or multiply-substituted with fluorine, chlorine, cyano, alkyl or alkoxy, preferably with fluorine, methyl, ethyl, propyl, butyl, methoxy, ethoxy, propoxy, butoxy or cyano.

Especially preferred are 1,4-phenylene residues.

Examples of preferred phenylene residues are 1,3- or, 1,4-phenylene, 4- or 5-methyl-1,3-phenylene, 4- or 5-methoxy-1,3-phenylene, 4- or 5-ethyl-1,3-phenylene, 4- or 5-ethoxy-1,3-phenylene, 2- or 3-methyl-1,4-phenylene, 2- or 3-ethyl-1,4-phenylene, 2- or 3-propyl-1,4-phenylene, 2- or 3-butyl-1,4-phenylene, 2- or 3-methoxy-1,4-phenylene, 2- or 3-ethoxy-1,4-phenylene, 2- or 3-propoxy-1,4-phenylene, 2- or 3-butoxy-1,4-phenylene, 2,3-, 2,6- or 3,5-dimethyl-1,4-phenylene, 2,6- or 3,5-dimethoxy-1,4-phenylene, 2- or 3-fluoro-1,4-phenylene, 2,3-, 2,6- or 3,5-difluoro-1,4-phenylene, 2- or 3-chloro-1,4-phenylene, 2,3-, 2,6-or 3,5-dichloro-1,4-phenylene, 2- or 3-cyano-1,4-phenylene, and the like.

Preferred polymer materials of the present invention consist of compounds of formula I in which

| | |
|---|---|
| ring A | signifies phenylene which is unsubstituted or optionally substituted with fluorine, chlorine, cyano, alkyl or alkoxy, pyridine-2,5-diyl, pyrimidine-2,5-diyl, cyclohexane-1,4-diyl; |
| ring B | signifies phenylene which is unsubstituted or optionally substituted with fluorine, chlorine, cyano, alkyl or alkoxy, pyridine-2,5-diyl, pyrimidine-2,5-diyl, 1,4- or 2,6-naphthylene, cyclohexane-1,4-diyl; |
| $Y^1, Y^2$ | each independently signify a single covalent bond, —$CH_2CH_2$—, —O—, —$CH_2$—O—, —O—$CH_2$—, —CO-O— or —O—OC—; |
| m, n | each independently signify 0 or 1; |
| ring C | signifies phenylene which is unsubstituted or optionally substituted with fluorine, chlorine, cyano, alkyl or alkoxy, or pyrimidine-2,5-diyl, pyridine-2,5-diyl, 2,5-furanylene, 1,4- or 2,6-naphthylene; |
| Z | signifies —O— and |
| D | signifies a straight-chain or branched alkyl group with 1 to 20, especially with 1 to 12, carbon atoms or a cycloalkyl residue with 5 or 6 ring atoms which is optionally substituted with alkyl or alkoxy, especially with methyl or methoxy, and |
| $M^1$ and $S^1$ | have the significance given above. |

Especially preferred polymer materials consist of compounds of formula I in which n=0 and

| | |
|---|---|
| ring B | signifies phenylene which is unsubstituted or optionally substituted with fluorine, chlorine, cyano, alkyl or alkoxy, pyridine-2,5-diyl, pyrimidine-2,5-diyl, cyclohexane-1,4-diyl; |
| $Y^2$ | signifies a single covalent bond, —CO—O— or —O—OC—; |

| | |
|---|---|
| m | signifies 0 or 1; |
| ring C | signifies phenylene which is unsubstituted or optionally substituted with fluorine, chlorine, cyano, alkyl or alkoxy, or 1,4- or 2,6-naphthylene; |
| Z | signifies —O— and |
| D | signifies a straight-chain or branched alkyl group with 1 to 12 carbon atoms and $M^1$ and $S^1$ have the significance given above. |

The present invention provides copolymer compositions in which repeating units of formula Ia are present, Ia

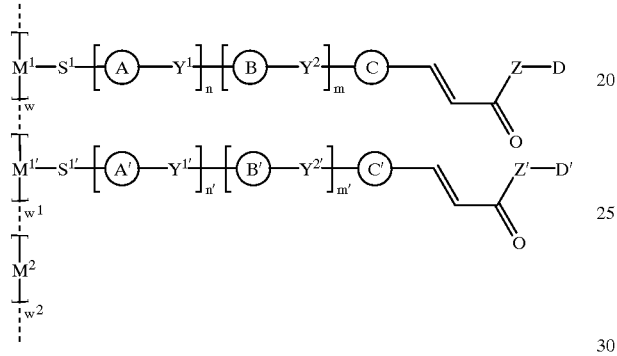

wherein
$M^1$, $M^{1'}$ each independently signify a repeating monomer unit from the group; acrylate, methacrylate, 2-chloroacrylate, 2-phenylacrylate; optionally N-lower alkyl substituted acrylamide, methacrylamide, 2-chloroacrylamide and 2-phenylacrylamide; vinyl ether, vinyl ester, styrene derivative, siloxane;

$S^1$, $S^{1'}$ each independently signify spacer units such as, for example, a single covalent bond, a straight-chain or branched alkylene grouping represented hereinafter by —$(CH_2)_r$—, as well as —$(CH_2)_r$—O—, —$(CH_2)_r$—O—$(CH_2)_s$—, —$(CH_2)_r$—O—$(CH_2)_s$—O—, —$(CH_2)_r$—CO—, —$(CH_2)_r$—CO—O—, —$(CH_2)_r$—O—CO—, —$(CH_2)_r$—$NR^2$—, —$(CH_2)_r$—CO—$NR^2$—, —$(CH_2)_r$—$NR^2$—CO—, —$(CH_2)_r$—$NR^2$—CO—O— or —$(CH_2)_r$—$NR^2$—CO—$NR^3$—, which is optionally mono- or multiply substituted with fluorine, chlorine or cyano and in which r and s are each a whole number of 1 to 20, with the proviso that r+s 20, and $R^2$ and $R^3$ each independently signify hydrogen or lower alkyl;

rings A, A' each independently signify phenylene which is unsubstituted or optionally substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl, piperazine-1,4-diyl;

rings B, B' each independently signify phenylene which is unsubstituted or optionally substituted with fluorine, chlorine, cyano, alkyl or alkoxy, pyridine-2,5-diyl, pyrimidine-2,5-diyl, 1,4- or 2,6-naphthylene, 1,3-dioxane-2,5-diyl, cyclohexane-1,4-diyl;

$Y^1$, $Y^2$, $Y^{1'}$, $Y^{2'}$ each independently signify a single covalent bond, —$(CH_2)_t$—, —O—, —CO—, —CO—O—, —O—OC—, —$NR^4$—, —CO—$NR^4$—, —$R^4N$—CO—, —$(CH_2)_u$—O—, —O—$(CH_2)_u$—, —$(CH_2)_u$—$NR^4$— or —$NR^4$—$(CH_2)_u$—, in which $R^4$, $R^{4'}$ each independently signify hydrogen or lower alkyl;

t, t' each independently signify a whole number of 1 to 4;

u, u' each independently signify a whole number of 1 to 3;

m, n, m', n' each independently signify 0 or 1;

rings C, C' each independently signify phenylene which is unsubstituted or optionally substituted with fluorine, chlorine, cyano, alkyl or alkoxy, or pyrimidine-2,5-diyl, pyridine-2,5-diyl, 2,5-thiophenylene, 2,5-furanylene, 1,4- or 2,6-naphthylene;

Z, Z' each independently signify —O— or —$NR^5$—, in which $R^5$ signifies hydrogen or lower alkyl, or a second group of formula D, in which D, D' each independently signify a straight-chain or branched alkyl group with 1 to 20 carbon atoms which is optionally substituted with fluorine or chlorine, a cycloalkyl residue with 3 to 8 ring atoms which is optionally substituted with fluorine, chlorine, alkyl or alkoxy.

$M^2$ signifies a repeating monomer unit from the group; acrylate, methacrylate, 2-chloroacrylate, 2-phenylacrylate; optionally N-lower alkyl substituted acrylamide, methacrylamide, 2-chloroacrylamide and 2-phenylacrylamide; vinyl ether, vinyl ester; straight-chain or branched alkyl esters of acrylic or methacrylic acid, allyl esters of acrylic or methacrylic acid, alkyl vinyl ethers or esters, phenoxyalkyl acrylates or phenoxyalkyl methacrylates, phenylalkyl acrylates or phenylalkyl methacrylates, hydroxyalkyl acrylates or hydroxyalkyl methacrylates with alkyl residues of 1 to 20, preferably 1 to 10, especially however with 1 to 6, carbon atoms; acrylonitrile, methacrylonitrile, styrene, 4-methylstyrene, siloxane; and w, w and $w^2$ are molar fractions of the comonomers with $0<w<1$, $0<w^1<1$ and $0<w^2\leq 0.5$.

Preferred are copolymer compositions with repeating units of formula Ia, wherein $M^1$ and $S^1$ as well as $M^{1'}$ and $S^{1'}$ and $M^2$ are as defined as above; and rings A, A' each independently signify phenylene which is unsubstituted or optionally substituted with fluorine, chlorine, cyano, alkyl or alkoxy, pyridine-2,5-diyl, pyrimidine-2,5-diyl, cyclohexane-1,4-diyl;

rings B, B' each independently signify phenylene which is unsubstituted or optionally substituted with fluorine, chlorine, cyano, alkyl or alkoxy, pyridine-2,5-diyl, pyrimidine-2,5-diyl, 1,4- or 2,6-naphthylene or cyclohexane-1,4-diyl;

$Y^1$, $Y^2$, $Y^{1'}$, $Y^{2'}$ each independently signify a single covalent bond, —$CH_2CH_2$—, —O—, —$CH_2$—O—, —O—$CH_2$—, —CO—O— or —O—OC—;

m, n, m', n' each independently signify 0 or 1;

rings C, C' each independently signify phenylene which is unsubstituted or optionally substituted with fluorine, chlorine, cyano, alkyl or alkoxy, or pyrimidine-2,5-diyl, pyridine-2,5-diyl, 2,5-furanylene or 1,4- or 2,6-naphthylene;

Z, Z' signify —O— and

D, D' each independently signify a straight-chain or branched alkylene group with 1 to 20, carbon atoms, preferably 1 to 12 carbon atoms or a cycloalkyl residue with 5 to 6 ring atoms which is optionally substituted with alkyl or alkoxy, especially with methyl or methoxy; and w, $w^1$ and $w^2$ are molar fractions of the comonomers with $0<w<1$, $0<w^1<1$ and $0<w^2\leq 0.5$.

Especially preferred are copolymer compositions with repeating units of formula Ia, wherein n and n' signify 0 and $M^1$ and $S^1$ as well as $M^{1'}$ and $S^{1'}$ and $M^2$ are as above; and rings B, B' each independently signify phenylene which is unsubstituted or optionally substituted with fluorine, chlorine, cyano, alkyl or alkoxy, pyridine-2,5-diyl, pyrimidine-2,5-diyl or cyclohexane-1,4-diyl;

$Y^2$, $Y^{2'}$ each independently signify a single covalent bond, —CO—O— or —O—OC—;

m, m' each independently signify 0 or 1;

n, n' signify 0;

rings C, C' each independently signify phenylene which is unsubstituted or optionally substituted with fluorine, chlorine, cyano, alkyl or alkoxy or 1,4- or 2,6-naphthylene;

Z, Z' signifiy —O— and

D, D' each independently signify a straight-chain or branched alkyl group with 1 to 12 carbon atoms; and w, $w^1$ and $w^2$ are molar fractions of the comonomers with $0<w<1$, $0<w^1<1$ and $0<w^2\leq 0.5$.

One such compound of the formula Ia can be prepared according to Example 3, namely poly [1-[2-[4-[(E)-2-methoxycarbonyl-vinyl]-phenoxy]-ethoxycarbonyl]-1-methyl-ethylene-co-1-[2-[4-[(E)-2-propoxycarbonyl-vinyl]-phenoxy]-ethoxycarbonyl]-1-methyl-ethylene-co-1-[2-hydroxy-ethoxycarbonyl]-1-methyl-ethylene (Example 3).

Further preferred copolymer compositions of formula I containing structures which are usual in polymer chemistry consist of compounds of the formula Ib, Ib

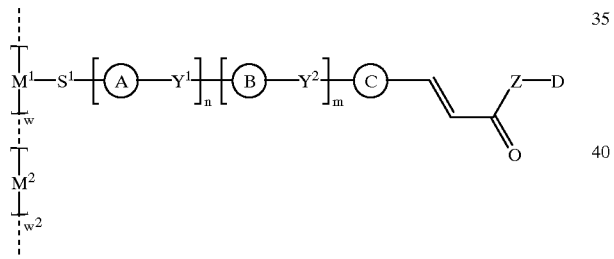

wherein $M^1$, $M^2$, $S^1$, A, B, C, D, Z, $Y^1$, $Y^2$, m and n are as defined above: and w and $w^2$ are molar fractions of the comonomers with $0<w<1$ and $0<w^2\leq 0.5$.

Preferred are copolymer compositions with repeating units of formula Ib, wherein $M^1$, $M^2$ and $S^1$ are as defined above; and ring A signifies phenylene which is unsubstituted or optionally substituted with fluorine, chlorine, cyano, alkyl or alkoxy, pyridine-2,5-diyl, pyrimidine-2,5-diyl, cyclohexane-1,4-diyl;

ring B signifies phenylene which is unsubstituted or optionally substituted with fluorine, chlorine, cyano, alkyl or alkoxy, pyridine-2,5-diyl, pyrimidine-2,5-diyl, 1,4- or 2,6-naphthylene or cyclohexane-1,4-diyl;

$Y^1$, $Y^2$ each independently signify a single covalent bond, —CH$_2$CH$_2$—, —O—, —CH$_2$—O—, —O—CH$_2$—, —CO—O— or —O—OC—;

m, n each independently signify 0 or 1;

ring C signifies phenylene which is unsubstituted or optionally substituted with fluorine, chlorine, cyano, alkyl or alkoxy, or pyrimidine-2,5-diyl, pyridine-2,5-diyl, 2,5-furanylene or 1,4- or 2,6-naphthylene;

Z signifies —O— and

D signifies a straight-chain or branched alkyl group with 1 to 20 carbon atoms, preferably 1 to 12 carbon atoms or a cycloalkyl residue with 5 to 6 ring atoms which is optionally substituted with alkyl or alkoxy, especially with methyl or methoxy; and w and $w^2$ are molar fractions of the comonomers with $0<w<1$ and $0<w^2\leq 0.5$.

Especially preferred are copolymer compositions with repeating units of formula Ib, wherein n signifies 0 and $M^1$, $M^2$ and $S^1$ are as defined above; and ring B signifies phenylene which is unsubstituted or optionally substituted with fluorine, chlorine, cyano, alkyl or alkoxy, pyridine-2,5-diyl, pyrimidine-2,5-diyl or cyclohexane-1,4-diyl;

$Y^2$ signifies a single covalent bond, —CO—O— or —O—OC—;

m signifies 0 or 1;

n signifies 0;

ring C signifies phenylene which is unsubstituted or optionally substituted with fluorine, chlorine, cyano, alkyl or alkoxy or 1,4- or 2,6-naphthylene;

Z signifies —O— and

D signifies a straight-chain or branched alkyl group with 1 to 12 carbon atoms. and w and $w^2$ are molar fractions of the comonomers with $0<w<1$ and $0<w^2\leq 0.5$.

One such preferred compounds with structures of formula Ib which are usual in polymer chemistry are described in Example 7, namely poly [1-[6-[4-[4-[(E)-2-methoxycarbonyl-vinyl]-phenoxycarbonyl]-phenoxy]-hexyloxycarbonyl]-1-methyl-ethylene-co-1-[2-ethylhexyloxycarbonyl]-1-methyl-ethylene] (Example 7);

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-ethoxycarbonyl-1-methyl-ethylene] (Example 7);

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-ethylhexyloxycarbonyl-1-methyl-ethylene] (Example 7).

Polymer compositions of the present invention are also copolymer compositions of formula I consisting of compounds with repeating units of formula Ic, Ic

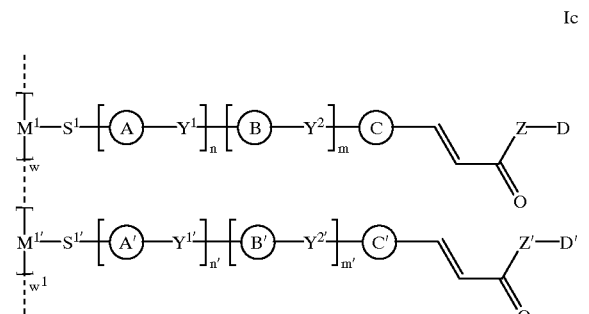

wherein $M^1$, $S^1$, A, B, C, D, Z, $Y^1$, $Y^2$, m and n as well as $M^{1'}$, $S^{1'}$, A', B', C', D', Z', $Y^{1'}$, $Y^{2'}$, m' and n' are as defined above; and w and $w^1$ are molar fractions of the comonomers with $0<w<1$ and $0<w^1\leq 1$.

Preferred are copolymer compositions with repeating units of formula Ic, wherein $M^1$ and $S^1$ as well as $M^{1'}$ and $S^{1'}$ are as defined above; and rings A, A' each independently signify phenylene which is unsubstituted or optionally substituted with fluorine, chlorine, cyano, alkyl or alkoxy, pyridine-2,5-diyl, pyrimidine-2,5-diyl, cyclohexane-1,4-diyl;

rings B, B' each independently signify phenylene which is unsubstituted or optionally substituted with fluorine, chlorine, cyano, alkyl or alkoxy, pyridine-2,5-diyl, pyrimidine-2,5-diyl, 1,4- or 2,6-naphthylene or cyclohexane-1,4-diyl;

$Y^1$, $Y^2$, $Y^{1'}$, $Y^{2'}$ each independently signify a single covalent bond, —CH$_2$CH$_2$—, —O—, —CH$_2$—O—, —O—CH$_2$—, —CO—O— or —O—OC—;

m, n, m', n' each independently signify 0 or 1;

rings C, C' each independently signify phenylene which is unsubstituted or optionally substituted with fluorine, chlorine, cyano, alkyl or alkoxy, or pyrimidine-2,5-diyl, pyridine-2,5-diyl, 2,5-furanylene or 1,4- or 2,6-naphthylene;

Z, Z' signify —O— and

D, D' each independently signify a straight-chain or branched alkyl group with 1 to 20, carbon atoms, preferably 1 to 12 carbon atoms or a cycloalkyl residue with 5 to 6 ring atoms which is optionally substituted with alkyl or alkoxy, especially with methyl or methoxy; and w and $w^1$ are molar fractions of the comonomers with $0<w<1$ and $0<w^1<1$.

Especially preferred are copolymer compositions with repeating units of formula Ic, wherein n and n' signify 0 and $M^1$ and $S^1$ as well as $M^{1'}$ and $S^{1'}$ are as defined above; and rings B, B' each independently signify phenylene which is unsubstituted or optionally substituted with fluorine, chlorine, cyano, alkyl or alkoxy, pyridine-2,5-diyl, pyrimidine-2,5-diyl or cyclohexane-1,4-diyl;

$Y^2$, $Y^{2'}$ each independently signify a single covalent bond, —CO—O— or —O—OC—;

m, m' each independently signify 0 or 1;

n, n' signify 0;

rings C, C' each independently signify phenylene which is unsubstituted or optionally substituted with fluorine, chlorine, cyano, alkyl or alkoxy or 1,4- or 2,6-naphthylene;

Z, Z' signifiy —O— and

D, D' each independently signify a straight-chain or branched alkyl group with 1 to 12 carbon atoms; and w and $w^1$ are molar fractions of the comonomers with $0<w<1$ and $0<w^1<1$.

One such preferred compound is described in Example 9, namely poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene] (Example 9).

Preferred are copolymer compositions of the formula Ia.

Especially preferred are compositions of the formula Ib and Ic.

Quite especially preferred are homopolymer compositions.

Concerning the homopolymers compositions with repeating units of formula I are preferred,

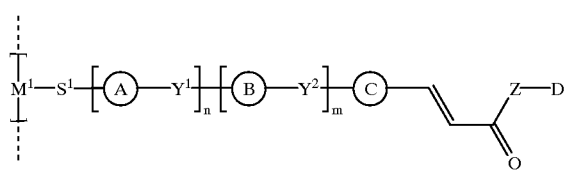

wherein $M^1$, $S^1$, A, B, C, D, Z, $Y^1$, $Y^2$, m and n are as defined above.

One such preferred homopolymer is poly [1-[3-[4-[4'-[(E)-2-methoxycarbonyl-vinyl]-biphenyl-4-yl]-cyclohexyl]-propoxycarbonyl]-1-methyl-ethylene] (Example 6).

Especially preferred are homopolymer compositions with repeating units of formula I, wherein $M^1$ and $S^1$ are as defined as above; and ring A signifies phenylene which is unsubstituted or optionally substituted with fluorine, chlorine, cyano, alkyl or alkoxy, pyridine-2,5-diyl, pyrimidine-2,5-diyl, cyclohexane-1,4-diyl;

ring B signifies phenylene which is unsubstituted or optionally substituted with fluorine, chlorine, cyano, alkyl or alkoxy, pyridine-2,5-diyl, pyrimidine-2,5-diyl, 1,4- or 2,6-naphthylene or cyclohexane-1,4-diyl;

$Y^1$, $Y^2$ each independently signify a single covalent bond, —CH$_2$CH$_2$—, —O—, —CH$_2$—O—, —O—CH$_2$—, —CO—O— or —O—OC—;

m, n each independently signify 0 or 1;

ring C signifies phenylene which is unsubstituted or optionally substituted with fluorine, chlorine, cyano, alkyl or alkoxy, or pyrimidine-2,5-diyl, pyridine-2,5-diyl, 2,5-furanylene or 1,4- or 2,6-naphthylene;

Z signifies —O— and

D signifies a straight-chain or branched alkyl group with 1 to 20 carbon atoms, preferably 1 to 12 carbon atoms or a cycloalkyl residue with 5 to 6 ring atoms which is optionally substituted with alkyl or alkoxy, especially with methyl or methoxy.

Especially preferred are homopolymer compositions with repeating units of formula I, wherein n signifies 0 and $M^1$ and $S^1$ are as defined above; and ring B signifies phenylene which is unsubstituted or optionally substituted with fluorine, chlorine, cyano, alkyl or alkoxy, pyridine-2,5-diyl, pyrimidine-2,5-diyl or cyclohexane-1,4-diyl;

$Y^2$ signifies a single covalent bond, —CO—O— or —O—OC—;

m signifies 0 or 1;

n signifies 0;

ring C signifies phenylene which is unsubstituted or optionally substituted with fluorine, chlorine, cyano, alkyl or alkoxy or 1,4- or 2,6-naphthylene;

Z signifies —O— and

D signifies a straight-chain or branched alkyl group with 1 to 12 carbon atoms.

Especially preferred homopolymers include

Poly [1-[4-[(E)-2-methoxycarbonyl-vinyl]-phenoxycarbonyl]-1-methyl-ethylene] (Example 1);

poly [1-[4-[(E)-2-methoxycarbonyl-vinyl]-phenylaminocarbonyl]-1-methyl-ethylene] (Example 1);

poly [1-[2-[4-[(E)-2-methoxycarbonyl-vinyl]-phenoxy]-ethoxycarbonyl]-1-methyl-ethylene] (Examples 2 and 3);

poly [1-[6-[4-[2-methoxy-4-[(E)-2-methoxycarbonyl-vinyl]-phenoxycarbonyl]-phenoxy]-hexyloxycarbonyl]-1-methyl-ethylene] (Example 4);

poly [1-[6-[4-[4-[(E)-2-methoxycarbonyl-vinyl]-phenoxycarbonyl]-phenoxy]-hexyloxycarbonyl]-1-methyl-ethylene] (Example 4);

poly [oxy-[4-[4-[4-[(E)-2-methoxycarbonyl-vinyl]-phenoxy-carbonyl]-phenoxy]-butyl]-methyl-silylen] (Example 5);

poly [1-[2-[(E)-2-methoxycarbonyl-vinyl]-naphthalin-6-yloxycarbonyl]-1-methyl-ethylene] (Example 8).

The polymers of formula I are characterized by being readily accessible. The methods for the production will be known to a person skilled in the art.

The polymers of formula I can be prepared in principal according to two different processes. In addition to the direct polymerization of pre-finished monomers there exists the possibility of polymer-analogous reaction of reactive cinnamic acid derivatives with functional polymers.

For the direct polymerization, the monomers and the comonomers are firstly prepared separately from the individual components. The formation of the polymers is subsequently effected in a manner known per se under the influence of UV radiation or heat or by the action of radical or ionic catalysts. Potassium peroxodisulphate, dibenzoyl peroxide, azobisisobutyronitrile or di-tert.-butylperoxide are examples of radical initiators. Ionic catalysts are alkali-organic compounds such as phenyllithium or naphthylsodium or Lewis acids such as $BF_3$, $AlCl_3$, $SnCl_3$ or $TiCl_4$. The monomers can be polymerized in solution, suspension, emulsion or substance.

In the second process a polymer of formula I can also be produced in a polymer-analogous reaction from a pre-finished functional polymer and a suitable functionalized cinnamic acid derivative. Many known processes such as, for example, esterification, trans-esterification, amidation or the etherification are suitable for polymer-analogous reactions.

The etherification of hydroxycinnamic acid derivatives with polyhydroxyalkyl acrylates or polyhydroxyalkyl methacrylates in solution under the conditions of the Mitsunobu reaction has been found to be advantageous here. Thus, the reaction can be carried out, for example, in that all hydroxy groups are reacted (homopolymer) or in that after the reaction hydroxy groups are still free on the polymer, which can then be further functionalized in a further polymeranalogous reaction, by which means copolymers can be synthesized. An alternative possibility for the production of copolymers according to this process comprises using mixtures of different cinnamic acid derivatives.

The cinnamic acids are partially commercially available or can be obtained according to methods known in the literature such as, for example, the Knoevenagel reaction or the Wittig reaction from commercially available aldehydes or from cyano compounds which are obtained by previous reduction to the corresponding aldehydes. The cinnamic esters or amides can then be prepared from the cinnamic acids according to known esterification procedures.

After application of the polymer layer to a carrier the cinnamic acid units of formula I can be dimerized by irradiation with linear polarized light. By the spatially selective irradiation of the molecular units of formula I specially determined regions of a surface can now be directed and can also simultaneously be stabilized by the dimerization.

Thus, for the production of polymer orienting layers in regions which are limited selectively by area, a solution of the polymer material obtained can, for example, firstly be produced and can be spun in a spin-coating apparatus on to a carrier which is optionally coated with an electrode (for example, a glass plate coated with indium-tin oxide (ITO) such that homogeneous layers of 0.05–50 μm thickness result. Subsequently, the regions to be oriented can be exposed e.g. to a mercury high-pressure lamp, a xenon lamp or a pulsed UV laser using a polarizer and optionally a mask in order to form structures. The duration of the exposure depends on the output of the individual lamps and can vary from a few minutes to several hours. The dimerization can, however, also be effected by irradiating the homogeneous layer using filters which let through e.g. only the radiation which is suitable for the cross-linking reaction.

The polymers in accordance with the invention are illustrated in more detail by the following Examples. In the Examples hereinafter Tg signifies the glass temperature, ε signifies the molar decadic absorption coefficient, G signifies a glassy solidification, C signifies the crystalline phase, S signifies the smectic phase, N signifies the nematic phase and I signifies the isotropic phase, p signifies the number of repeating units resulting in polymers having a molecular weight $M_W$ between 1,000 and 5,000,000, preferably however between 5,000 and 2,000,000, especially advantageously however between 10,000 and 1,000,000, w, $w^1$ and $w^2$ are molar fractions of the comonomers with $0<w<1.0<w^1<1$ and $0<w^2\leq 0.5$.

The following examples are illustrative of the invention.

EXAMPLE 1

Poly [1-[4-[(E)-2-methoxycarbonyl-vinyl]-phenoxycarbonyl]-1-methyl-ethylene]

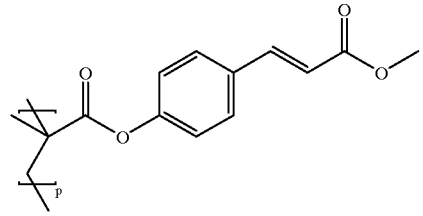

0.5 g (2.03 mmol) of 4-[(E)-2-methoxycarbonyl-vinyl]-phenyl 2-methyl-acrylate and 1.67 mg (0.01 mmol) of 2,2'-azo-bis-isobutyronitrile (AIBN) were dissolved in 4.1 ml of tetrahydrofuran (THF). The solution was flushed with a weak stream of argon for 15 minutes. Subsequently, the reaction vessel was sealed air-tight and heated to 60° C. After 24 hours the vessel was opened, the solution was diluted with 4 ml of THF and added dropwise to 800 ml of diethyl ether at room temperature while stirring vigourously. The separated polymer was filtered off and dried at 60° C. in a water-jet vacuum. For further purification, the polymer was dissolved in 10 ml of dichloromethane and again precipitated in 80 ml of diethyl ether. This procedure was repeated until monomer was no longer detected by thin-layer chromatography. Filtration and drying at 60° C. in a vacuum gave 0.37 g of poly [1-[4-[(E)-2-methoxycarbonyl-vinyl]-phenoxy-carbonyl]-1-methyl-ethylene] as a white powder with a glass stage at $T_g$=145° C. and an absorption maximum of $\lambda_{max}$. (in $CH_2Cl_2$)=275.2 nm ($\epsilon$=21430 l/mol cm).

The 4-[(E)-2-methoxycarbonyl-vinyl]-phenyl 2-methyl-acrylate used as the starting material was prepared according to the following procedure:

Methyl 3-(4-hydroxyphenyl)-acrylate

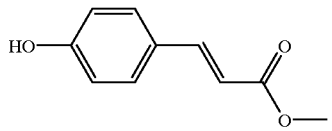

51.2 g (312 mmol) of p-coumaric acid were dissolved in 330 ml of methanol and treated with 10 ml of concentrated sulphuric acid. The solution was heated under reflux for 2 hours. Subsequently the majority of the methanol (about 200 ml) was distilled off and the residue remaining behind was poured into 1.3 l of ice-water. The separated ester was filtered off under suction and washed in succession with cold water, with a small amount of cold $NaHCO_3$ solution and again with cold water. Drying at 50° C. in a water-jet vacuum gave 51.1 g of methyl 3-(4-hydroxyphenyl)-acrylate in the form of a light brownish coloured powder.

4-[(E)-2-Methoxycarbonyl-vinyl]-phenyl 2-methyl-acrylate

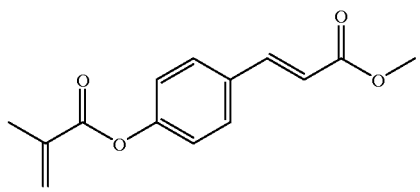

10.5 g (59 mmol) of methyl 3-(4-hydroxy-phenyl)-acrylate were dissolved in 170 ml of tetrahydrofuran and treated in succession with 9.1 ml (65 mmol) of triethylamine and 0.079 g (0.65 mmol) of 4-dimethylamino-pyridine (DMAP). 6.8 g (65 mmol) of methacryloyl chloride were added dropwise to the solution, cooled to about 15° C., over a period of minutes. The reaction batch was stirred at room temperature overnight and subsequently filtered over a thin silica gel layer. The silica gel layer was rinsed thoroughly with THF. After evaporation of the solvent the crude product was recrystallized from about 200 ml of ethanol. It was filtered off, dried and recrystallized once more from ethanol. Filtration and drying at 50° C. in a water-jet vacuum gave 10.3 g of 4-[(E)-2-methoxycarbonyl-vinyl]-phenyl 2-methyl-acrylate as white crystals with a melting point of 76–80° C. and an absorption maximum of $\lambda_{max}$. (in $CH_2Cl_2$)=281.7 nm ($\epsilon$=24290 l/mol cm).

The following polymers can be synthesized in an analogous manner:

Poly [1-[4-[(E)-2-ethoxycarbonyl-vinyl]-phenoxycarbonyl]-1-methyl-ethylene];

poly [1-[4-[(E)-2-propoxycarbonyl-vinyl]-phenoxycarbonyl]-1-methyl-ethylene];

poly [1-[4-[(E)-2-butoxycarbonyl-vinyl]-phenoxycarbonyl]-1-methyl-ethylene];

poly [1-[4-[(E)-2-hexyloxycarbonyl-vinyl]-phenoxycarbonyl]-1-methyl-ethylene];

poly [1-[4-[(E)-2-methoxycarbonyl-vinyl]-phenoxycarbonyl]-1-methyl-ethylene-co-1-[4-[(E)-2-hexyloxycarbonyl-vinyl]-phenoxycarbonyl]-1-methyl-ethylene];

poly [1-[4-[(E)-2-methoxycarbonyl-vinyl]-phenoxycarbonyl]-1-methyl-ethylene-co-1-[4-[(E)-2-octyloxycarbonyl-vinyl]-phenoxycarbonyl]-1-methyl-ethylene];

poly [1-[4-[(E)-2-ethoxycarbonyl-vinyl]-phenoxycarbonyl]-1-methyl-ethylene-co-1-[4-[(E)-2-pentyloxycarbonyl-vinyl]-phenoxycarbonyl]-1-methyl-ethylene];

poly [1-[4-[(E)-2-methoxycarbonyl-vinyl]-phenylaminocarbonyl]-1-methyl-ethylene], $T_g$=207° C.;

poly [1-[4-[(E)-2-butoxycarbonyl-vinyl]-phenylaminocarbonyl]-1-methyl-ethylene];

poly [1-[4-[(E)-2-methoxycarbonyl-vinyl]-phenylaminocarbonyl]-1-methyl-ethylene-co-1-[4-[(E)-2-pentyloxycarbonyl-vinyl]-phenylaminocarbonyl]-1-methyl-ethylene];

poly [1-[4-[(E)-2-methylaminocarbonyl-vinyl]-phenoxycarbonyl]-1-methyl-ethylene];

poly [1-[4-[(E)-2-dimethylaminocarbonyl-vinyl]-phenoxycarbonyl]-1-methyl-ethylene];

poly [1-[4-[4-[(E)-2-methoxycarbonyl-vinyl]-phenyl]-phenoxycarbonyl]-1-methyl-ethylene];

poly [1-[4-[4-[(E)-2-methoxycarbonyl-vinyl]-phenyl]-cyclo-hexyloxycarbonyl]-1-methyl-ethylene];

poly [1-[4-[4-[(E)-2-methoxycarbonyl-vinyl]-phenyl]-cyclo-hexylmethoxycarbonyl]-1-methyl-ethylene].

EXAMPLE 2

Poly [1-(2-[4-[(E)-2-methoxycarbonyl-vinyl]-phenoxy]-ethoxycarbonyl]-1-methyl-ethylene]

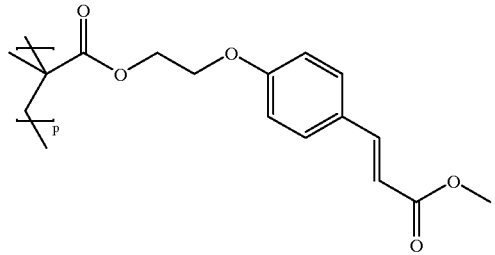

0.555 g (1.91 mmol) of 2-[4-[(E)-2-methoxycarbonyl-vinyl]-phenoxy]-ethyl 2-methyl-acrylate and 3.14 mg (0.019 mmol) of 2,2'-azo-bis-isobutyronitrile (AIBN) were dissolved in 3.8 ml of tetrahydrofuran (THF). The solution was flushed with a weak stream of argon for 15 minutes. Subsequently, the reaction vessel was sealed air-tight and heated to 55° C. After 24 hours the vessel was opened, the solution was diluted with 4 ml of THF and added dropwise to 800 ml of diethyl ether at room temperature while stirring vigourously. The separated polymer was filtered off and dried at 60° C. in a water-jet vacuum. For further purification, the polymer was dissolved in 10 ml of dichloromethane and again precipitated in 800 ml of diethyl ether. This procedure was repeated until monomer was no longer detectable by thin-layer chromatography. Filtration and drying at 60° C. in a vacuum gave 0.34 g of poly [1-[2-[4-[(E)-2-methoxycarbonyl-vinyl]-phenoxy]-ethoxycarbonyl]-

1-methylethylene] as a white powder with a glass stage at $T_g=92°$ C. and an absorption maximum of $\lambda_{max}$. (in $CH_2Cl_2$)=296.3 nm ($\epsilon$=21680 l/mol cm).

The 2-[4-[(E)-2-methoxycarbonyl-vinyl]-phenoxy]-ethyl 2-methyl-acrylate used as the starting material was prepared according to the following procedure:

Methyl (E)-3-[4-[2-hydroxyethoxy]-phenyl]-acrylate

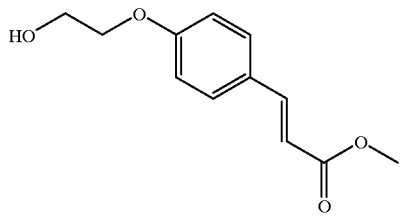

30 g (168 mmol) of methyl 3-(4-hydroxyphenyl)-acrylate (Example 1), 29 g (210 mmol) of anhydrous $K_2CO_3$ and a spatula tip of KI were placed in 200 ml of dimethylformamide. 14.91 g (185 mmol) of 2-chloroethanol were added dropwise at 85° C. within 5 minutes while stirring. The batch was stirred at 85° C. for a further 3 days. Subsequently, the salts were filtered off and the filtrate was concentrated to dryness in a water-jet vacuum. 16.1 g of methyl (E)-3-[4-[2-hydroxyethoxy]-phenyl]-acrylate were obtained in the form of white crystals after recrystallization from i-propanol.

2-[4-[(E)-2-Methoxycarbonyl-vinyl]-phenoxy]-ethyl 2-methyl-acrylate

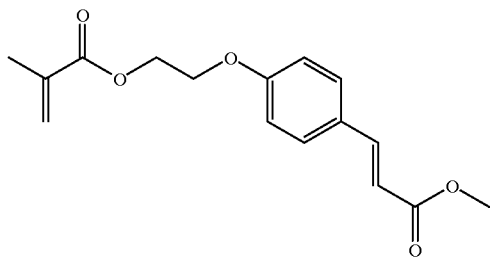

2.56 g (30 mmol) of methacrylic acid in 10 ml of THF were slowly added dropwise to a solution of 6 g (27 mmol) of methyl (E)-3-[4-[2-hydroxyethoxy]-phenyl]-acrylate, 5.85 g (28.3 mmol) of N,N'-dicyclohexylcarbodiimide (DCC) and 0.37 g (3 mmol) of 4-dimethylamino-pyridine in 80 ml of tetrahydrofuran (THF). The batch was stirred at room temperature overnight. In order to complete the reaction there were added firstly a further 1.46 g (7.1 mmol) of DCC and, after stirring for one hour, a further 0.5 g (5.9 mmol) of methacrylic acid. The batch was stirred for a further 24 hours, filtered and the filtrate was extracted 3 times each time with 200 ml of 5% acetic acid and 200 ml of water. The ether phase was dried over $Na_2SO_4$, evaporated and the residue was recrystallized from cyclohexane. Subsequently, the still slightly impure product was filtered over a thin silica gel layer (eluent: diethyl ether/hexane= 1:1). This gave 8.3 g of 2-[4-[(E)-2-methoxycarbonyl-vinyl]-phenoxy]-ethyl 2-methyl-acrylate as a white powder with a melting point of 81–82° C. and an absorption maximum of $\lambda_{max}$. (in $CH_2Cl_2$)=306.5 nm ($\epsilon$=23675 l/mol cm).

The following polymers can be synthesized in an analogous manner:

Poly [1-[2-[4-[(E)-2-ethoxycarbonyl-vinyl]-phenoxy]-ethoxycarbonyl]-1-methyl-ethylene];

poly [1-methyl-1-[2-[4-[(E)-2-propoxycarbonyl-vinyl]-phenoxy]-ethoxycarbonyl]-ethylene], $T_g=64°$ C.;

poly [1-[2-[3-[(E)-2-methoxycarbonyl-vinyl]-phenoxy]-ethoxycarbonyl]-1-methyl-ethylene];

poly [1-[2-(6-methoxy-3-[(E)-2-methoxycarbonyl-vinyl]-phenoxy]-ethoxycarbonyl]-1-methyl-ethylene];

poly [1-[2-[2-methoxy-4-[(E)-2-methoxycarbonyl-vinyl]-phenoxy]-methoxycarbonyl]-1-methyl-ethylene];

poly [1-[2-[2-ethoxy-4-[(E)-2-methoxycarbonyl-vinyl]-phenoxy]-methoxycarbonyl]-1-methyl-ethylene];

poly [1-[2-[2-fluoro-4-[(E)-2-methoxycarbonyl-vinyl]-phenoxy]-methoxycarbonyl]-1-methyl-ethylene];

poly [1-[2-[4-[(E)-2-methoxycarbonyl-vinyl]-2-methyl-phenoxy]-methoxycarbonyl]-1-methyl-ethylene];

poly [1-[1,1-dimethyl-2-[4-[(E)-2-methoxycarbonyl-vinyl]-phenoxy]-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-methyl-1-[2-[4-[(E)-2-propoxycarbonyl-vinyl]-phenoxy]-ethoxycarbonyl]-ethylene] (9:1), $T_g=88°$ C.;

poly [1-[2-[4-[(E)-2-methoxycarbonyl-vinyl]-phenoxy]-ethoxycarbonyl]-1-methyl-ethylene-co-1-methyl-1-[2-[4-[(E)-2-propoxycarbonyl-vinyl]-phenoxy]-ethoxycarbonyl]-ethylene] (1:1), $T_g=76°$ C.;

poly [1-[2-[4-[(E)-2-methoxycarbonyl-vinyl]-phenoxy]-ethoxycarbonyl]-1-methyl-ethylene-co-1-[2-[4-[(E)-2-butoxycarbonyl-vinyl]-phenoxy]-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-(2-methyl-butoxy)-carbonyl-vinyl]-phenoxy]-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-octyloxycarbonyl-vinyl]-phenoxy]-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-dodecyloxycarbonyl-vinyl]-phenoxy]-ethoxycarbonyl]-1-methyl-ethylene];

poly [1-[2-[4-[(E)-2-methoxycarbonyl-vinyl]-2-methyl-phenoxyl-ethoxycarbonyl]-1-methyl-ethylene];

poly [1-[2-[2-methoxy-4-[(E)-2-methoxycarbonyl-vinyl]-phenoxy]-ethoxycarbonyl]-1-methyl-ethylene];

poly [1-[2-[4-4-[(E)-2-methoxycarbonyl-vinyl]-phenyl]-phenoxy]-ethoxycarbonyl]-1-methyl-ethylen];

poly [1-[6-[4-4-[(E)-2-methoxycarbonyl-vinyl]-phenyl]-phenoxy]-hexyloxycarbonyl]-1-methyl-ethylene];

poly [1-[2-[4-4-[(E)-2-methoxycarbonyl-vinyl]-phenyl]-cyclohexyloxy]-ethoxycarbonyl]-1-methyl-ethylene];

poly [1-[4-[4-4-[(E)-2-methoxycarbonyl-vinyl]-phenyl]-cyclohexyloxy]-butoxycarbonyl]-1-methyl-ethylene];

poly [1-[2-[4-[5-[(E)-2-methoxycarbonyl-vinyl]-pyridin-2-yl]-phenoxy]-ethoxycarbonyl]-1-methyl-ethylene];

poly [1-[2-[2-[4-[(E)-2-methoxycarbonyl-vinyl]-phenyl]-pyrimidin-5-yloxy]-ethoxycarbonyl]-1-methyl-ethylene];

poly [1-[2-[6-[(E)-2-methoxycarbonyl-vinyl]-naphthalin-2-yloxy]-ethoxycarbonyl]-1-methyl-ethylene];

poly [1-[2-[4-[(E)-2-methoxycarbonyl-vinyl]-naphthalin-1-yloxy]-ethoxycarbonyl]-1-methyl-ethylene];

Poly [1-[8-[4-[(E)-2-methoxycarbonyl-vinyl]-naphthalin-1-yloxy]-octyloxycarbonyl]-1-methyl-ethylene].

EXAMPLE 3

Poly [1-[2-[4-[(E)-2-methoxycarbonyl-vinyl]-phenoxy]-ethoxycarbonyl]-1-methyl-ethylene] by Polymer-analogous Etherification According to Mitsunobu

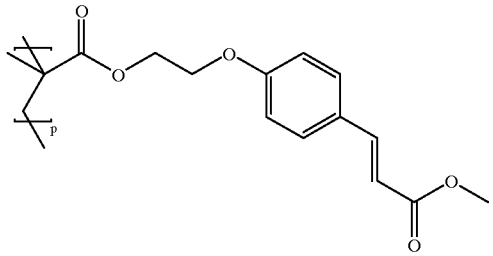

2.5 g (4.05 mmol) of a stock solution of poly (2-hydroxyethyl methacrylate) (21 wt. % in DMA) were diluted 7.5 ml of dimethylacetamide (DMA) under argon. 2.32 g (8.8 mmol) of triphenylphosphine and 1.44 g (8.1 mmol) of methyl 3-(4-hydroxyphenyl)-acrylate were dissolved in the reaction batch at room temperature while stirring. The solution was cooled to 0° C. 1.4 ml (8.8 mmol) of diethyl azodicarboxylate (DEAD) were added dropwise within 4 hours. The reaction batch was left at 0° C. for a further 15 minutes and then, after removal of the ice bath, stirred at room temperature for 15 hours. The reaction mixture was then added dropwise to about 900 ml of diethyl ether while stirring vigourously. The separated polymer was filtered off and dried at 60° C. in a water-jet vacuum. For purification, the residue was dissolved in 10 ml of dichloromethane and again precipitated in diethyl ether. This procedure was repeated until monomer was no longer detectable by thin-layer chromatography. Filtration and drying at 60° C. in a vacuum gave 0.93 g of poly [1-[2-[4-[(E)-2-methoxycarbonyl-vinyl]-phenoxy]-ethoxycarbonyl]-1-methyl-ethylene] as a white powder with a glass stage at $T_g=88°$ C. and an absorption maximum of $\lambda_{max}$ (in $CH_2Cl_2$)=296.6 nm ($\epsilon$=20610 l/mol cm).

The following polymers can be synthesized in an analogous manner:

Poly [1-[2-[4-[(E)-2-methoxycarbonyl-vinyl]-phenoxy]-ethoxycarbonyl]-1-methyl-ethylene-co-1-[2-hydroxyethoxycarbonyl]-1-methyl-ethylene], $T_g=90°$ C.;

poly [1-[2-[4-[(E)-2-ethoxycarbonyl-vinyl]-phenoxy]-ethoxycarbonyl]-1-methyl-ethylene-co-1-[2-hydroxyethoxycarbonyl]-1-methyl-ethylene];

poly [1-[2-[3-[(E)-2-methoxycarbonyl-vinyl]-phenoxy]-ethoxycarbonyl]-1-methyl-ethylene-co-1-[2-hydroxyethoxycarbonyl]-1-methyl-ethylene];

poly [1-[2-[3-[(E)-2-methoxycarbonyl-vinyl]-phenoxy]-ethoxycarbonyl]-1-methyl-ethylene-co-1-[2-hydroxyethoxycarbonyl]-1-methyl-ethylene (4:1), $T_g=73°$ C.;

poly [1-[2-[6-methoxy-3-[(E)-2-methoxycarbonyl-vinyl]-phenoxy]-ethoxycarbonyl]-1-methyl-ethylene-co-1-[2-hydroxyethoxycarbonyl]-1-methyl-ethylene];

poly [1-[2-[2-methoxy-4-[(E)-2-methoxycarbonyl-vinyl]-phenoxy]-ethoxycarbonyl]-1-methyl-ethylene], $T_g=84°$ C.;

poly [1-[4-[2-methoxy-4-[(E)-2-methoxycarbonyl-vinyl]-phenoxy]-butoxycarbonyl]-1-methyl-ethylene], $T_g=60°$ C.;

poly [1-[2-[2-methoxy-4-[(E)-2-methoxycarbonyl-vinyl]-phenoxy]-methoxycarbonyl]-1-methyl-ethylene-co-1-[2-hydroxy-ethoxycarbonyl]-1-methyl-ethylene];

poly [1-[2-[2-ethoxy-4-[(E)-2-methoxycarbonyl-vinyl]-phenoxy]-methoxycarbonyl]-1-methyl-ethylene-co-1-[2-hydroxyethoxycarbonyl]-1-methyl-ethylene];

poly [1-[2-[2-fluoro-4-[(E)-2-methoxycarbonyl-vinyl]-phenoxy]-methoxycarbonyl]-1-methyl-ethylene-co-1-[2-hydroxyethoxycarbonyl]-1-methyl-ethylene];

poly [1-[2-[4-[(E)-2-methoxycarbonyl-vinyl]-2-methyl-phenoxyl]-methoxycarbonyl]-1-methyl-ethylene-co-1-[2-hydroxyethoxycarbonyl]-1-methyl-ethylene];

poly [1-[1,1-dimethyl-2-[4-[(E)-2-methoxycarbonyl-vinyl]-phenoxy]-ethoxycarbonyl]-1-methyl-ethylene-co-1-[2-hydroxyethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-propoxycarbonyl-vinyl]-phenoxy]-ethoxycarbonyl]-1-methyl-ethylene-co-1-[2-hydroxy-ethoxycarbonyl]-1-methyl-ethylene] (15:3:7), $T_g=101°$ C.;

poly [1-[2-[4-[(E)-2-methoxycarbonyl-vinyl]-phenoxy]-ethoxycarbonyl]-1-methyl-ethylene-co-1-[2-[4-[(E)-2-propoxycarbonyl-vinyl]-phenoxy]-ethoxycarbonyl]-1-methyl-ethylene-co-1-[2-hydroxy-ethoxycarbonyl]-1-methyl-ethylene] (11:4:3), $T_g=94°$ C.;

poly [1-[2-[4-[(E)-2-methoxycarbonyl-vinyl]-phenoxy]-ethoxycarbonyl]-1-methyl-ethylene-co-1-[2-[4-[(E)-2-butoxycarbonyl-vinyl]-phenoxy]-ethoxycarbonyl]-1-methyl-ethylene-co-1-[2-hydroxy-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-(2-methylbutoxy)-carbonyl-vinyl]-phenoxy]-ethoxycarbonyl]-1-methyl-ethylene-co-1-[2-hydroxy-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-octyloxycarbonyl-vinyl]-phenoxy]-ethoxycarbonyl]-1-methyl-ethylene-co-1-[2-hydroxy-ethoxycarbonyl]-1-methyl-ethylene];

poly [1-[2-[4-[(E)-2-methoxycarbonyl-vinyl]-phenoxy]-ethoxycarbonyl]-1-methyl-ethylene-co-1-[2-[4-[(E)-2-dodecyloxycarbonyl-vinyl]-phenoxy]-ethoxycarbonyl]-1-methyl-ethylene-co-1-[2-hydroxy-ethoxycarbonyl]-1-methyl-ethylene];

poly [1-(2-[4-[(E)-2-methoxycarbonyl-vinyl]-2-methyl-phenoxy]-ethoxycarbonyl]-1-methyl-ethylene-co-1-[2-hydroxyethoxycarbonyl]-1-methyl-ethylene];

poly [1-[2-[2-methoxy-4-[(E)-2-methoxycarbonyl-vinyl]-phenoxy]-ethoxycarbonyl]-1-methyl-ethylene-co-1-[2-hydroxy-ethoxycarbonyl]-1-methyl-ethylene];

poly [1-[2-[4-[4-[(E)-2-methoxycarbonyl-vinyl]-phenyl]-phenoxy]-ethoxycarbonyl]-1-methyl-ethylene-co-1-[2-hydroxyethoxycarbonyl]-1-methyl-ethylene];

poly [1-[6-[4-[4-[(E)-2-methoxycarbonyl-vinyl]-phenyl]-phenoxy]-hexyloxycarbonyl]-1-methyl-ethylene];

poly [1-[2-[4-[4-[(E)-2-methoxycarbonyl-vinyl]-phenyl]-cyclohexyloxy]-ethoxycarbonyl]-1-methyl-ethylene-co-1-[2-hydroxyethoxycarbonyl]-1-methyl-ethylene];

poly [1-[4-[4-[4-[(E)-2-methoxycarbonyl-vinyl]-phenyl]-cyclohexyloxy]-butoxycarbonyl]-1-methyl-ethylene-co-1-[2-hydroxyethoxycarbonyl]-1-methyl-ethylene];

poly [1-[2-[4-[5-[(E)-2-methoxycarbonyl-vinyl]-pyridin-2-yl]-phenoxy]-ethoxycarbonyl]-1-methyl-ethylene-co-1-[2-hydroxyethoxycarbonyl]-1-methyl-ethylene];

poly [1-[2-[2-[4-[(E)-2-methoxycarbonyl-vinyl]-phenyl]-pyrimidin-5-yloxy]-ethoxycarbonyl]-1-methyl-ethylene-co-1-[2-hydroxy-ethoxycarbonyl]-1-methyl-ethylene];

poly [1-[2-[6-[(E)-2-methoxycarbonyl-vinyl]-naphthalen-2-yloxy]-ethoxycarbonyl]-1-methyl-ethylene-co-1-[2-hydroxyethoxycarbonyl]-1-methyl-ethylene];

poly [1-[2-[4-[(E)-2-methoxycarbonyl-vinyl]-naphthalen-1-yloxy]-ethoxycarbonyl]-1-methyl-ethylene-co-1-[2-hydroxyethoxycarbonyl]-1-methyl-ethylene];

poly [1-[8-[4-[(E)-2-methoxycarbonyl-vinyl]-naphthalen-1-yloxy]-octyloxycarbonyl]-1-methyl-ethylene-co-1-[2-hydroxyethoxycarbonyl]-1-methyl-ethylene].

EXAMPLE 4

Poly 1-[-6-[4-[2-methoxy-4-[(E)-2-methoxycarbonyl-vinyl]-phenoxycarbonyl]-phenoxy]-hexyloxycarbonyl]-1-methyl-ethylene]

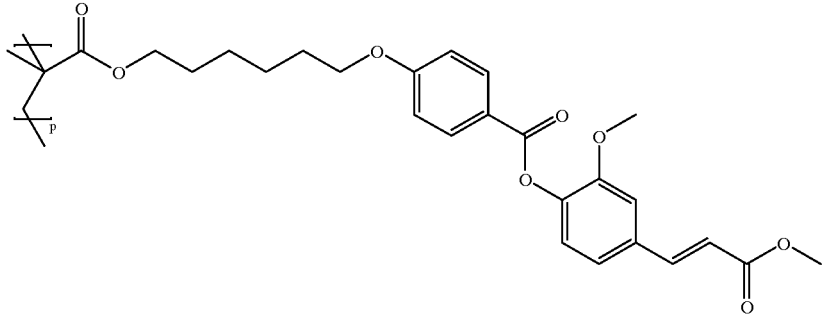

2.5 g (5 mmol) of 2-methoxy-4-[(E)-2-methoxycarbonyl-vinyl]-phenyl 4-[6-(2-methyl-acryloyloxy)-hexyloxy]-benzoate and 8.2 mg (0.05 mmol) of 2,2'-azo-bis-isobutyronitrile were dissolved in 10 ml of tetrahydrofuran (THF). The solution was flushed with a weak stream of argon for 30 minutes. Subsequently, the reaction vessel was sealed air-tight and heated to 55° C. After 24 hours the vessel was opened, the solution was diluted with 8 ml of THF and added dropwise to 1.6 l of ethanol at room temperature while stirring vigourously. The separated polymer was filtered off and dried at 50° C. in a water-jet vacuum. For further purification, the polymer was dissolved in about 25 ml of dichloromethane and again precipitated in 1.75 l of methanol. This procedure was repeated until monomer was no longer detectable by thin-layer chromatography. Filtration and drying at 50° C. in a water-jet vacuum gave 2.14 g of poly [1-[6-[4-[2-methoxy-4-[(E)-2-methoxycarbonyl-vinyl]-phenoxycarbonyl]-phenoxy]-hexyloxycarbonyl]-1-methyl-ethylene] with a molecular weight $M_W$ of 769 000 (gelpermeations-chromatography: THF, 35° C., polystyrolstandard), with a glass stage at $T_g$=74° C. and an absorption maximum of $\lambda_{max}$. (in $CH_2Cl_2$)=277.0 nm ($\epsilon$=31575 l/mol cm).

The 2-methoxy-4-[(E)-2-methoxycarbonyl-vinyl]-phenyl 4-[6-(2-methyl-acryloyloxy)-hexyloxy]-benzoate used as the starting material was prepared according to the following procedure:

4-(6-Hydroxy-hexyloxy)-benzoic acid

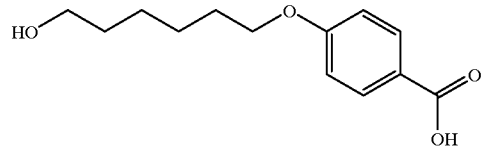

229.2 g (1.66 mol) of p-hydroxy-benzoic acid were dissolved in 600 ml of methanol and treated at 0° C. within 10 minutes with a solution of 151 g (3.77 mol) of NaOH in 480 ml of $H_2O$. 271.2 g (1.99 mol) of 6-chloro-hexanol were slowly added dropwise to this solution. Finally, 0.75 g of potassium iodide was added and the batch was boiled under reflux for 60 hours. For the working up, the yellow solution was poured into 3 l of $H_2O$ and treated with 10% HCl (about 600 ml) until a pH value of 1 had been achieved. The milky suspension was filtered over a large suction filter. The residue was sucked dry and recrystallized twice from about 1.5 l of ethanol. This gave 229.6 g of 4-(6-hydroxy-hexyloxy)-benzoic acid as a fine white powder; m.p. 136–141° C.

4-[6-(2-Methyl-acryloyloxy)-hexyloxy]-benzoic acid

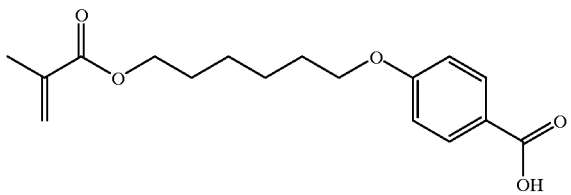

71.5 g (0.3 mol) of 4-(6-hydroxy-hexyloxy)-benzoic acid and 101.5 g (1.18 mol) of methacrylic acid were dissolved in 950 ml of chloroform. After the addition of 7.2 g (0.07 mol) of hydroquinone and 7.2 g (0.04 mol) of p-toluenesulphonic acid the batch was boiled under reflux on a water separator for 48 hours. The clear brown solution was subsequently evaporated, the residue was taken up in 1.5 l of diethyl ether, filtered and shaken five time with 300 ml of H$_2$O each time. The organic phase was dried over Na$_2$SO$_4$, evaporated and the residue was recrystallized twice from methanol. After drying at 40° C. in a water-jet vacuum 47.33 g of 4-[6-(2-methyl-acryloyloxy)-hexyloxy]-benzoic acid remained behind as a white powder; m.p. 83° C.

Methyl 4-hydroxy-3-methoxy-cinnamate

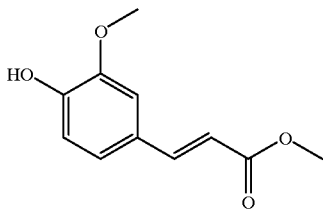

The preparation was effected analogously to Example 1 from 25 g (0.129 mol) of 4-hydroxy-3-methoxy-cinnamic acid and 180 ml of methanol with concentrated sulphuric acid as the catalyst. For purification, it was chromatographed on silica gel with dichloromethane/diethyl ether (19:1). This gave 21.78 g of methyl 4-hydroxy-3-methoxy-cinnamate as a pale yellow oil.

2-Methoxy-4-[(E)-2-methoxycarbonyl-vinyl]-phenyl 4-[6-(2-methyl-acryloyloxy)-hexyloxy]-benzoate 8.5 g (0.028 mol) of 4-[6-(2-methyl-acryloyloxy)-hexyloxy]-benzoate were treated with 6 ml of thionyl chloride and 3 drops of DMF and the mixture was heated to 90° C. for 2 hours. The excess thionyl chloride was completely removed firstly in a water-jet vacuum and subsequently in a high vacuum. The residual acid chloride was taken up in 20 ml of dichloromethane and slowly added dropwise at 0° C. to a solution of 5.25 g (0.025 mol) of methyl 4-hydroxy-3-methoxy-cinnamate and 4.25 ml of triethylamine in 25 ml of THF. The batch was stirred at room temperature overnight, filtered and the filtrate was evaporated to dryness. The residue was purified by column chromatography on silica gel with dichloromethane/diethyl ether (19:1) and subsequently by recrystallization from ethanol/THF. 6.31 g of 2-methoxy-4-[(E)-2-methoxycarbonyl-vinyl]-phenyl 4-[6-(2-methyl-acryloyloxy)-hexyloxy]-benzoate were isolated as a white powder; m.p. 92–94° C.

The following polymers can be synthesized in an analogous manner:

Poly [1-[6-[4-[4-[(E)-2-methoxycarbonyl-vinyl]-phenoxycarbonyl]-phenoxy]-hexyloxycarbonyl]-1-methyl-ethylene], Phase effect (° C.): G 64 LC1 135 LC2 164 l;

poly [1-[6-[4-[2-ethoxy-4-[(E)-2-methoxycarbonyl-vinyl]-phenoxycarbonyl]-phenoxy]-hexyloxycarbonyl]-1-methyl-ethylene] T$_g$=64° C.;

poly [1-[6-[4-[2-propoxy-4-[(E)-2-methoxycarbonyl-vinyl]-phenoxycarbonyl]-phenoxy]-hexyloxycarbonyl]-1-methyl-ethylene];

poly [1-[6-[4-[2-butoxy-4-[(E)-2-methoxycarbonyl-vinyl]-phenoxycarbonyl]-phenoxy]-hexyloxycarbonyl]-1-methyl-ethylene];

poly [1-[6-[4-[2-methyl-4-[(E)-2-methoxycarbonyl-vinyl]-phenoxycarbonyl]-phenoxy]-hexyloxycarbonyl]-1-methyl-ethylene];

poly [1-[4-[4-[2-methyl-4-[(E)-2-methoxycarbonyl-vinyl]-phenoxycarbonyl]-phenoxy]-butyloxycarbonyl]-1-methyl-ethylene];

poly [1-[2-[4-[2-methoxy-4-[(E)-2-methoxycarbonyl-vinyl]-phenoxycarbonyl]-phenoxy]-ethoxycarbonyl]-1-methyl-ethylene], T$_g$=119° C.;

poly [1-[3-[4-[2-methoxy-4-[(E)-2-methoxycarbonyl-vinyl]-phenoxycarbonyl]-phenoxy]-propoxycarbonyl]-1-methyl-ethylene], T$_g$=102° C.;

poly [1-[2-[2-methoxy-4-[(E)-2-methoxycarbonyl-vinyl]-phenoxycarbonyl]-phenoxy]-ethoxycarbonyl]-1-methyl-ethylene];

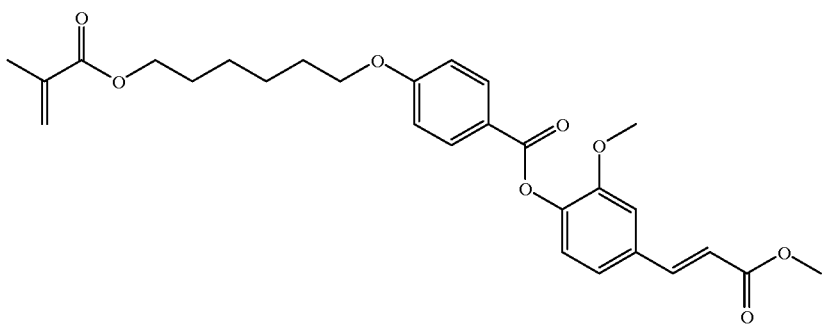

poly [1-[2-[2-methyl-4-[4-[(E)-2-methoxycarbonyl-vinyl]-phenoxycarbonyl]-phenoxy]-ethoxycarbonyl]-1-methyl-ethylene];

poly [1-6-[2-methoxy-4-[4-[(E)-2-methoxycarbonyl-vinyl]-phenoxycarbonyl]-phenoxy]-hexyloxycarbonyl]-1-methyl-ethylene];

poly [1-[6-[2-methyl-4-[4-[(E)-2-methoxycarbonyl-vinyl]-phenoxycarbonyl]-phenoxy]-hexyloxycarbonyl]-1-methyl-ethylene];

poly [1-[6-[4-[4-[2-methoxy-4-[(E)-2-methoxycarbonyl-vinyl]-phenoxycarbonyl]-phenyl]-phenoxy]-hexyloxycarbonyl]-1-methyl-ethylene];

poly [1-[6-[4-[4-[2-methoxy-4-[(E)-2-methoxycarbonyl-vinyl]-phenoxycarbonyl]-cyclohexyl]-cyclohexyloxy]-hexyloxycarbonyl]-1-methyl-ethylene].

EXAMPLE 5

Poly [oxy-1-[4-[4-[(E)-2-methoxycarbonyl-vinyl]-phenoxycarbonyl]-phenoxy]-butyl]-1-methyl-silylene]

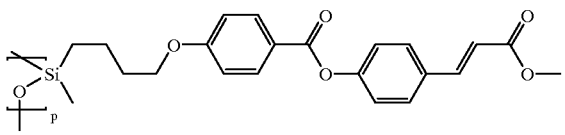

0.5 g (1.4 mmol) of 4-[(E)-2-methoxycarbonyl-vinyl]-phenyl 4-(but-3-enyloxy)-benzoate and 0.071 g of poly (methylhydrogensiloxane) were dissolved in 3 ml of toluene. The solution was flushed for 10 minutes with a weak stream of nitrogen through a septum on the reaction vessel. Subsequently, 8 μl of a platinum-divinyltetramethyldisiloxane complex solution were sprayed in to the reaction mixture at room temperature while stirring. The batch was stirred at 55° C. for 24 hours. Then, the polymer solution was added dropwise to 400 ml of ice-cooled n-hexane while stirring. The precipitated polymer was separated, dried, dissolved in about 5 ml of toluene and precipitated in 400 ml of methanol. This procedure was repeated twice. After drying in a high vacuum this gave 0.15 g of poly [oxy-1-[4-[4-[(E)- 2-methoxycarbonyl-vinyl]-phenoxycarbonyl]-phenoxy]-butyl]-1-methyl-silylene] as a white powder with the phase effect (° C.): G 35 S 194 I.

The 4-[(E)-2-methoxycarbonyl-vinyl]-phenyl 4-(but-3-enyloxy)-benzoate used as the starting material was prepared according to the following procedure:

4-(But-3-enyloxy)-benzoic acid

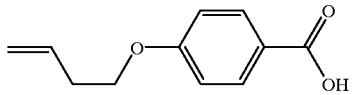

69.1 g (0.5 mol) of p-hydroxybenzoic acid were dissolved in 400 ml of ethanol and treated with a solution of 56.1 g (1 mol) of KOH in 250 ml of water. The reaction batch was heated under reflux. While so doing 74.26 g (0.55 mol) of 4-bromo-1-butene were slowly added dropwise. After 5 hours the ethanol was removed on a rotary evaporator. The aqueous phase was brought to a pH value of 10 with NaOH and extracted repeatedly with diethyl ether. The aqueous phase was poured into a mixture of 46 ml of concentrated HCl and 500 ml of ice-water. The separated acid was filtered off, washed with a small amount of water and recrystallized from methanol/water (2:1). After drying at 60° C. in a water-jet vacuum 40 g of 4-(but-3-enyloxy)-benzoic acid remained behind as a white powder; phase succession (° C.): C 120 N 141 I.

4-[(E)-2-Methoxycarbonyl-vinyl]-phenyl 4-(but-3-enyloxy)-benzoate

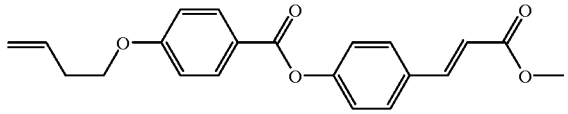

8.7 g (0.045 mol) of 4-(but-3-enyloxy)-benzoic acid were treated with 76 ml of thionyl chloride and 2 drops of DMF and boiled under reflux for 3.5 hours. The excess thionyl chloride was completely removed firstly in a water-jet vacuum and subsequently in a high vacuum. The residual acid chloride was taken up in 10 ml of dichloromethane and slowly added dropwise at 0° C. to a mixture of 7.59 g (0,042 mol) of methyl 3-(4-hydroxyphenyl)-acrylate (Example 1) and 6 ml of triethylamine in 40 ml of dichloromethane. The batch was stirred at room temperature overnight. The white precipitate in the reaction mixture was dissolved by the addition of dichloromethane. The organic phase was washed repeatedly with water, dried over $Na_2SO_4$ and evaporated to dryness. For purification, the residue was chromatographed on silica gel with dichloromethane and subsequently recrystallized from ethanol. 12.65 g of 4-[(E)-2-methoxycarbonyl-vinyl]-phenyl 4-(but-3-enyloxy)-benzoate were isolated as a white powder; phase succession (° C.): C 103 N138 I.

The following polymers can be synthesized in an analogous manner:

Poly [oxy-4-[4-[2-methoxy-4-[(E)-2-methoxycarbonyl-vinyl]-phenoxycarbonyl]-phenoxy]-butyl]-1-methyl-silylene]; $T_g$=47° C.;

poly [oxy-4-[4-[2-fuoro-4-[(E)-2-methoxycarbonyl-vinyl]-phenoxycarbonyl]-phenoxy]-butyl]-1-methyl-silylene];

poly [oxy-6-[4-[2-methyl-4-[(E)-2-methoxycarbonyl-vinyl]-phenoxycarbonyl]-phenoxyl-hexyl]-1-methyl-silylene];

poly [oxy-4-[4-[4-((E)-2-methoxycarbonyl-vinyl]-phenyl]-phenoxy]-butyl]-1-methyl-silylene];

poly [oxy-6-[6-[4-[(E)-2-methoxycarbonyl-vinyl]-phenyl]-cyclohexyloxy]-hexyl]-1-methyl-silylene];

poly [oxy-4-[4-[4-[(E)-2-methoxycarbonyl-vinyl]-phenoxycarbonyl]-phenoxy]-butyl]-methyl-silylene-co-oxy-4-[4-[4-[(E)- 2-hexyloxycarbonyl-vinyl]-phenoxycarbonyl]-phenoxy]-butyl]-methyl-silylene];

poly [oxy-4-[4-[4-[(E)-2-methoxycarbonyl-vinyl]-phenoxycarbonyl]-phenoxy]-butyl]-methyl-silylene-co-oxy-6-[4-[4-[(E)-2-methoxycarbonyl-vinyl]-phenoxycarbonyl]-phenoxy]-hexyl]-methyl-silylene];

poly [oxy-4-[4-[4-[(E)-2-methoxycarbonyl-vinyl]-phenoxycarbonyl]-phenoxy]-butyl]-methyl-silylene-co-dimethyl-oxy-silylene;

poly [oxy-4-[4-[4-[(E)-2-methoxycarbonyl-vinyl]-phenoxy-carbonyl]-phenoxy]-butyl]-methyl-silylene-co-oxy-4-[4-[4-[(E)-2-butoxycarbonyl-vinyl]-phenoxycarbonyl]-phenoxy]-butyl]-methyl-silylen-co-dimethyl-oxy-silylene].

EXAMPLE 6

Poly [1-[3-[4-[4'-[(E)-2-methoxycarbonyl-vinyl]-biphenyl-4-yl]-cyclohexyl]-propoxycarbonyl]-1-methyl-ethylene]

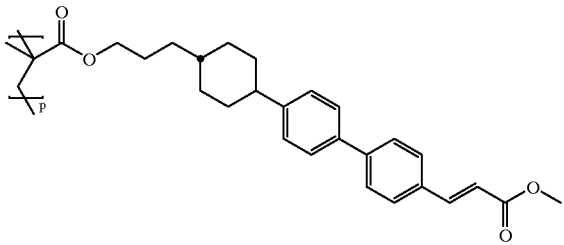

The polymerization of 3-[4-[4'-[(E)-2-methoxycarbonyl-vinyl]-biphenyl-4-yl]-cyclohexyl]-propyl trans-2-methyl-acrylate to poly[1-[3-[4-[4'-[(E)-2-methoxycarbonyl-vinyl]-biphenyl-4-yl]-cyclo-hexyl]-propoxycarbonyl]-1-methyl-ethylene] was effected analogously to Example 1. The polymer has the following phase succession (° C.): G 156 C 208 I.

The 3-[4-[4'-[(E)-2-methoxycarbonyl-vinyl]-biphenyl-4-yl]-cyclohexyl]-propyl trans-2-methyl-acrylate used as the starting material was prepared according to the following procedure:

trans-4'-[4-(3-Hydroxy-propyl)-cyclohexyl]-biphenyl-4-carbonitril

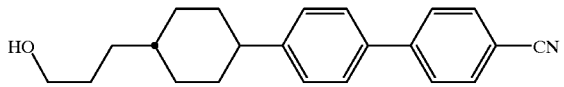

A solution of 12 g of trans-4'-[4-(3-oxo-propyl)-cyclohexyl]-biphenyl-4-carbonitrile (preparation: Mol. Cryst. Liq. Cryst. 1985, Vol. 131, 327) in 100 ml methanol/ether (9:1) was added dropwise at 0° C. within 5 minutes to a suspension of 1.39 g of sodium borohydride in 30 ml of methanol/ether (9:1). After 45 minutes a further 1 g of sodium borohydride was added. After a further hour the reaction was interrupted and the mixture was partitioned between methylene chloride and 1N hydrochloric acid. Thereupon, the organic phase was washed several times with water, dried over magnesium sulphate, filtered and evaporated. Crystallization from ethyl acetate/methylene chloride gave 11.5 g of trans-4'-[4-(3-hydroxy-propyl)-cyclohexyl]-biphenyl-4-carbonitrile as yellowish crystals.

trans-4'-[4-(3-Hydroxy-propyl)-cyclohexyl]-biphenyl-4-carboxaldehyde

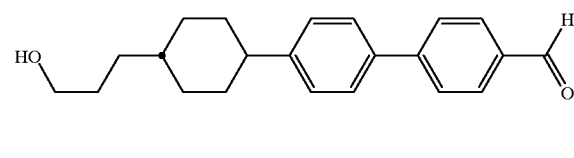

38.5 ml of a diisobutyl aluminium hydride solution (20% in toluene) was added dropwise at 0° C. within 10 minutes to a suspension of 11.5 g of trans-4'-[4-(3-hydroxy-propyl)-cyclohexyl]-biphenyl-4-carbonitrile in 150 ml of toluene. Then, the reaction mixture was warmed slowly to room temperature and left to react for a further 3.5 hours. Subsequently, 1N hydrochloric acid was slowly added dropwise, the reaction mixture was stirred for 1 hour and thereupon partitioned between water and methylene chloride. Thereafter, the organic phase was washed repeatedly with water, dried over magnesium sulphate, filtered and evaporated. Crystallization from ethyl acetate/methylene chloride gave 9.9 g of trans-4'-[4-(3-hydroxy-propyl)-cyclohexyl]-biphenyl-4-carboxaldehyde as pale yellow crystals.

trans-4'-[4-[3-(2-Methyl-acryloyloxy)-propyl]-cyclohexyl]-biphenyl-4-carboxaldehyde

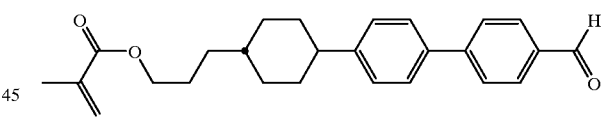

Firstly 9.4 ml of triethylamine and then 2.63 ml of methanesulphonyl chloride were added dropwise at −25° C. to a solution of 2.9 ml of methacrylic acid in 30 ml of tetrahydrofuran. Thereafter, the mixture was stirred at −25° C. for 1 hour and then a solution of 9.9 g of trans-4'-[4-(3-hydroxy-propyl)-cyclohexyl]-biphenyl-4-carboxaldehyde and 1.1 g of 4-dimethylamino-pyridine in 50 ml of tetrahydrofuran was added dropwise. Thereafter, the mixture was left to react at 0° C. for 2.5 hours and then at room temperature for 18 hours. Thereupon, the reaction mixture was filtered over Celite, the filtrate was partitioned between ether and water, the ether phase was dried over magnesium sulphate and evaporated. This gave 11.5 g of crude trans-4'-[4-[3-(2-methyl-acryloyloxy)-propyl]-cyclohexyl]-biphenyl-4-carboxaldehyde in solid form.

3-[4-[4'-[(E)-2-Methoxycarbonyl-vinyl]-biphenyl-4-yl]-cyclohexyl]-propyl trans-2-methyl-acrylate

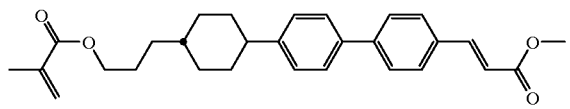

27.6 ml of a 1.6N butyl lithium solution were added dropwise at 0° C. within 10 minutes to a solution of 6.4 ml of trimethylphosphonacetate in 50 ml of dry tetrahydrofuran. The mixture was stirred at 0° C. for 1.5 hours and thereafter a solution of 11.5 g of crude trans-4'-[4-[3-(2-methyl-acryloyloxy)-propyl]-cyclo-hexyl]-biphenyl-4-carboxaldehyde in 50 ml of dry tetrahydrofuran was added dropwise at the same temperature within 5 minutes. Subsequently, the mixture was warmed slowly to room temperature and left to react for 15 hours. The reaction mixture was then partitioned between methylene chloride and 1N hydrochloric acid, the organic phase was washed with saturated sodium bicarbonate solution and water, dried over magnesium sulphate and evaporated. Chromatography on silica gel with ethyl acetate/hexane (1:9) and subsequent repeated recrystallization from hexane/ethyl acetate gave 0.71 g of 3-[4-[4'-[(E)-2-methoxycarbonyl-vinyl]-biphenyl-4-yl]-cyclohexyl]-propyl trans-2-methyl-acrylate as colourless crystals.

EXAMPLE 7

Poly [1-[6-[4-[4-[(E)-2-methoxycarbonyl-vinyl]-phenoxycarbonyl]-phenoxy]-hexyloxycarbonyl]-1-methyl-ethylene-co-1-[2-ethylhexyloxycarbonyl]-1-methyl-ethylene]

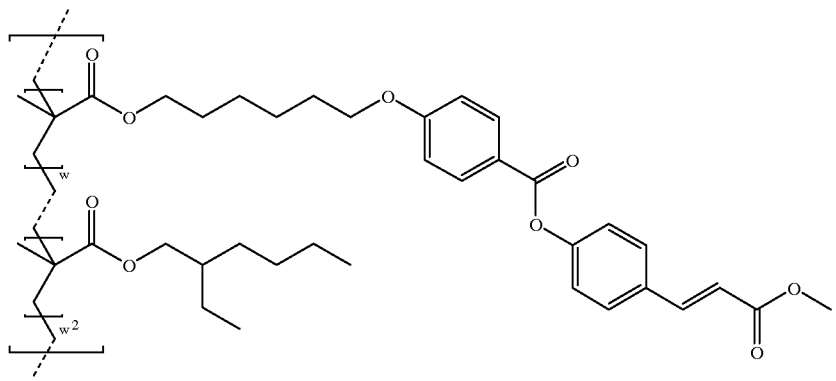

0.43 g (0.91 mmol) of [(E)-2-methoxycarbonyl-vinyl]-phenyl 4-[6-(2-methyl-acryloyloxy)-hexyloxy]-benzoate 0.01 g (0.05 mmol) of 2-ethylhexyl methacrylate (Fluka 64072) and 1.6 mg (0.0095 mmol) of 2,2'-azo-bis-isobutyronitrile were dissolved in 1.9 ml of tetrahydrofuran (THF). The solution was flushed with a weak stream of argon for 30 minutes. Subsequently, the reaction vessel was sealed air-tight and heated to 55° C. After 15 hours the vessel was opened, the solution was diluted with 2 ml of THF and added dropwise to 0.9 l of diethyl ether at room temperature while stirring vigorously. The separated polymer was filtered off and dried at 50° C. in a water-jet vacuum. For further purification, the polymer was dissolved in about 5 ml of dichloromethane and again precipitated in 0.9 l of diethyl ether. This procedure was repeated until monomer was no longer detected by thin-layer chromatography. Filtration and drying at 50° C. in a water-jet vacuum gave 0.385 g of poly [1-[6-[4-[4-[(E)-2-methoxycarbonyl-vinyl]-phenoxycarbonyl]-phenoxy]-hexyloxycarbonyl]-1-methyl-ethylene-co-1-[2-ethylhexyloxy-carbonyl]-1-methyl-ethylene] (18:1) with the phase sequence (° C.): G 42 S 205 I.

The [(E)-2-methoxycarbonyl-vinyl]-phenyl 4-[6-(2-methyl-acryloyloxy)hexyloxy]-benzoate was prepared analogously to 2-methoxy-4-[(E)-2-methoxycarbonyl-vinyl]-phenyl 4-[6-(2-methyl-acryloyloxy)-hexyloxy]-benzoate (Example 4).

The following polymers can be synthesized in an analogous manner:

Poly [1-[6-[4-[4-[(E)-2-methoxycarbonyl-vinyl]-phenoxycarbonyl]-phenoxy]-hexyloxycarbonyl]-1-methyl-ethylene-co-1-[2-ethylhexyloxycarbonyl]-1-methyl-ethylene] (9:1), phase sequence (° C.): G 41 LC 200 I;

poly [1-[6-[4-[4-[(E)-2-methoxycarbonyl-vinyl]-phenoxycarbonyl]-phenoxy]-hexyloxycarbonyl]-1-methyl-ethylene-co-1-[2-ethylhexyloxycarbonyl]-1-methyl-ethylene] (4:1);

poly [1-[3-[4-[4-[(E)-2-methoxycarbonyl-vinyl]-phenoxycarbonyl]-phenoxy]-propoxycarbonyl]-1-methyl-ethylene-co-1-[2-ethylhexyloxycarbonyl]-ethylene];

poly [1-[2-[4-[4-[(E)-2-methoxycarbonyl-vinyl]-phenoxycarbonyl]-phenoxy]-ethoxycarbonyl]-1-methyl-ethylene-co-1-hexyloxycarbonyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-methoxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-ethoxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-propoxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-butyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-pentyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-hexyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-octyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-dodecyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-octadecyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-allyloxycarbonyl-1-methyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-phenyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-methoxycarbonyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-butyloxycarbonyl-ethylene];

poly [1-[6-[4-[4-[(E)-2-methoxycarbonyl-vinyl]-phenoxycarbonyl]-phenoxy]-hexyloxycarbonyl]-1-methyl-ethylene-co-1-cyano-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-methoxycarbonyl-1-methyl-ethylene];

poly [1-[6-[4-[2-methoxy-4-[(E)-2-methoxycarbonyl-vinyl]-phenoxycarbonyl]-phenoxyl-hexyloxycarbonyl]-1-methyl-ethylene-co-1-ethoxycarbonyl-1-methyl-ethylene] (19:1), $T_g$=76° C.;

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-propoxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-methyl-propoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-butyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-pentyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-hexyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-ethylhexyloxycarbonyl-1-methyl-ethylene] (20:1), $T_g$=73° C.;

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-octyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-dodecyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-octadecyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-allyloxycarbonyl-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-phenoxyethoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-phenylethoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-phenyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-cyano-ethylene];

poly [1-[4-[(E)-2-methoxycarbonyl-vinyl]-phenoxycarbonyl]-1-methyl-ethylene-co-1-phenyl-ethylene];

poly [1-[4-[(E)-2-methoxycarbonyl-vinyl]-phenoxycarbonyl]-1-methyl-ethylene-co-1-methoxycarbonyl-1-methyl-ethylene];

poly [1-[4-[(E)-2-methoxycarbonyl-vinyl]-phenoxycarbonyl]-1-methyl-ethylene-co-1-propoxycarbonyl-1-methyl-ethylene];

poly [1-[4-[(E)-2-methoxycarbonyl-vinyl]-phenoxycarbonyl]-1-methyl-ethylene-co-1-hexyloxycarbonyl-1-methyl-ethylene];

poly [1-[2-[4-((E)-2-methoxycarbonyl-vinyl]-phenoxy]-ethoxycarbonyl]-1-methyl-ethylene-co-1-methoxycarbonyl-1-methyl-ethylene];

poly [1-[2-[4-[(E)-2-methoxycarbonyl-vinyl]-phenoxy]-ethoxycarbonyl]-1-methyl-ethylene-co-1-butyloxycarbonyl-1-methyl-ethylene];

poly [1-[2-[4-[(E)-2-methoxycarbonyl-vinyl]-phenoxy]-ethoxycarbonyl]-1-methyl-ethylene-co-1-octyloxycarbonyl-1-methyl-ethylene];

poly [1-[4-[4-[(E)-2-methoxycarbonyl-vinyl]-phenoxy]-butyloxycarbonyl]-1-methyl-ethylene-co-1-methoxycarbonyl-1-methyl-ethylene];

poly [1-[6-[4-[(E)-2-methoxycarbonyl-vinyl]-phenoxy]-hexyloxycarbonyl]-1-methyl-ethylene-co-1-hexyloxycarbonyl-1-methyl-ethylene];

poly [1-[2-[2-methoxy-4-[(E)-2-methoxycarbonyl-vinyl]-phenoxy]-ethoxycarbonyl]-1-methyl-ethylene-co-1-butyloxycarbonyl-1-methyl-ethylene];

poly [1-[4-[2-methoxy-4-[(E)-2-methoxycarbonyl-vinyl]-phenoxy]-butyloxycarbonyl]-1-methyl-ethylene-co-1-pentyloxycarbonyl-1-methyl-ethylene].

EXAMPLE 8

Poly [1-[2-[(E)-2-methoxycarbonyl-vinyl]-naphthalen-6-yloxycarbonyl]-1-methyl-ethylene]

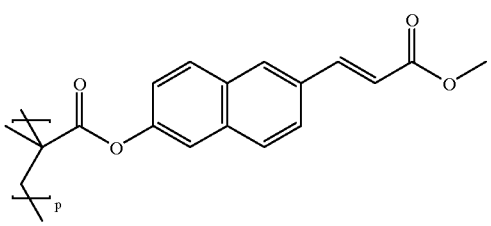

0.9 g (3.04 mmol) of (E)-2-(2-methoxycarbonyl-vinyl)-naphthalin-6-yl 2-methyl-acrylate and 3.7 mg (0.02 mmol) of 2,2'-azo-bis-isobutyronitrile were dissolved in 4.5 ml of tetrahydrofuran (THF). The solution was flushed with a weak stream of argon for 30 minutes. Subsequently, the reaction vessel was sealed air-tight and heated to 60° C. After 9 hours the vessel was opened, the solution was diluted with 2 ml of THF and added dropwise to 1 l of methanol at room temperature while stirring vigorously. The separated polymer was filtered off and dried at 40° C. in a vacuum. For further purification, the polymer was dissolved in about 6 ml of THF and again precipitated in 1 l of methanol. This procedure was repeated until monomer was no longer detectable by thin-layer chromatography. Filtration and drying at 40° C. in a vacuum gave 0.15 g of poly [1-[2-[(E)-2-methoxycarbonyl-vinyl]-naphthalen-6-yloxycarbonyl]-1-methyl-ethylene with a molecular weight $M_W$ of 624 000 (gelpermeations-chromatography: THF, 35° C., polystyrol-standard) and with absorption maxima at $\lambda_{max}$(CHCl$_3$)= 261.9 nm; 270.9 nm and 303.7 nm.

The (E)-2-(2-methoxycarbonyl-vinyl)-naphthalen-6-yl 2-methyl-acrylate used as the starting material was prepared according to the following procedure.

Methyl (E)-3-(6-hydroxy-naphthalen-2-yl)-acrylate

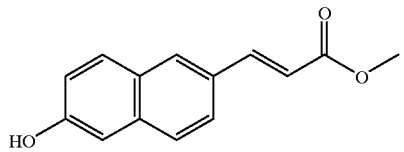

5 g (22.4 mmol) of 6-bromo-2-naphthol, 6 ml (67.2 mmol) of methyl acrylate, 100 mg (0.45 mmol) of palladium acetate and 25 ml of triethylamine were placed in a flask gassed with nitrogen. After the addition of 545 mg (1.79 mmol) of tri-(o-tolyl)-phosphine the reaction mixture was boiled under reflux overnight. After 15 hours the reaction was interrupted and the mixture was partitioned between ethyl acetate and water. The organic phase was back-washed three times with water and the aqueous phases were each individually back-washed twice with ethyl acetate. The combined organic phases were dried over magnesium sulphate, filtered over Celite and evaporated completely in a vacuum. Chromatography on silica gel with toluene/ethyl acetate (3:2) and subsequent recrystallization from ethyl acetate gave 3.65 g of methyl (E)-3-(6-hydroxy-naphthalen-2-yl)-acrylate.

(E)-2-(2-Methoxycarbonyl-vinyl)-naphthalen-6-yl 2-methyl-acrylate

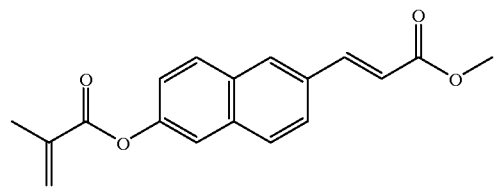

0.89 g (3.9 mmol) of methyl (E)-3-(6-hydroxy-naphthalen-2-yl)-acrylate, a spatula tip of BHT and 0.66 ml of triethylamine were dissolved in 10 ml of THF. After cooling to 0° C. a solution of 0.39 ml (4.07 mmol) of methacryloyl chloride in 4 ml of THF was added dropwise within 30 minutes. The white suspension was stirred at 0° C. for a further hour and then partitioned in ether and water. The organic phase was back-washed twice with water and the aqueous phases were back-washed twice with diethyl ether. The combined organic phases were dried over magnesium sulphate, filtered over Celite and evaporated completely in a vacuum. The crude product was recrystallized from a mixture of 5 ml of hexane and 20 ml of toluene. This gave 0.92 g of white (E)-2-(2-methoxycarbonyl-vinyl)-naphthalen-6-yl 2-methyl-acrylate.

EXAMPLE 9

Poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene]

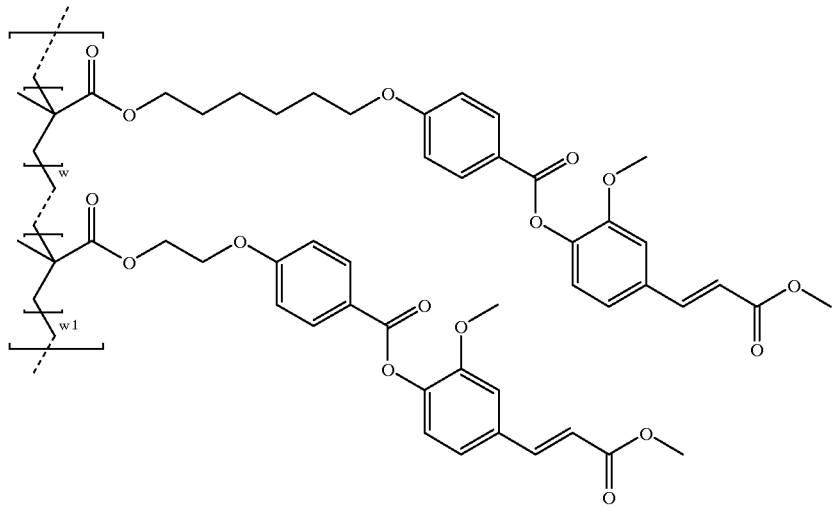

0.224 g (0.45 mmol) of 2-methoxy-4-[(E)-2-methoxycarbonyl-vinyl]-phenyl 4-[6-(2-methyl-acryloyloxy)-hexyloxy]-benzoate, 0.198 g (0.45 mmol) of 2-methoxy-4-[(E)-2-methoxycarbonyl-vinyl]-phenyl 4-[2-(2-methyl-acryloyloxy)-ethoxy]-benzoate and 1.5 mg (0.009 mmol) of 2,2'-azo-bis-isobutyronitrile were dissolved in 1.8 ml of tetrahydrofuran (THF). The solution was flushed with a weak stream of argon for 30 minutes. Subsequently, the reaction vessel was sealed air-tight and heated to 55° C. After 6 hours the vessel was opened, the solution was diluted with 2 ml of THF and added dropwise to 0.9 l of diethyl ether at room temperature while stirring vigorously. The separated polymer was filtered off and dried at 40° C. in a water-jet vacuum. For further purification, the polymer was dissolved in about 5 ml of dichloromethane and again precipitated in 0.9 l of diethyl ether. This procedure was repeated until monomer was no longer detectable by thin-layer chromatography. Filtration and drying at 40° C. in a water-jet vacuum gave 0.26 g of poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene] (1:1) with a glass stage at $T_g$=92° C. and an absorption maximum of $\lambda_{max}$ (in $CH_2Cl_2$)=276.5 nm.

The 2-methoxy-4-[(E)-2-methoxycarbonyl-vinyl]-phenyl 4-[6-(2-methyl-acryloyloxy)-hexyloxy]-benzoate and the 2-methoxy-4-[(E)-2-methoxycarbonyl-vinyl]-phenyl 4-[2-(2-methyl-acryloyloxy)-ethoxy]-benzoate were prepared according to the procedure described in Example 4.

The following polymers can be synthesized in an analogous manner:

Poly [1-[3-[4-[2-methoxy-4-[(E)-2-methoxycarbonyl-vinyl]-phenoxycarbonyl]-phenoxy]-propoxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene];

poly [1-[3-[4-[2-methoxy-4-[(E)-2-methoxycarbonyl-vinyl]-phenoxycarbonyl]-phenoxy]-propoxycarbonyl]-1-methyl-ethylene-co-1-[6-[4-[2-methoxy-4-[(E)-2-methoxycarbonyl-vinyl]-phenoxycarbonyl]-phenoxy]-hexyloxycarbonyl]-1-methyl-ethylene];

poly [1-[2-[4-[2-methoxy-4-[(E)-2-methoxycarbonyl-vinyl]-phenoxycarbonyl]-phenoxy]-ethoxycarbonyl]-1-methyl-ethylene-co-1-[8-[4-[2-methoxy-4-[(E)-2-methoxycarbonyl-vinyl]-phenoxycarbonyl]-phenoxy]-octyloxycarbonyl]-1-methyl-ethylene];

poly [1-[6-[4-[2-ethoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co- 1-[2-[4-[4-[(E)-2-methoxycarbonyl-vinyl]-phenoxycarbonyl]-phenoxy]-ethoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-fluoro-4-[(E)-2-methoxycarbonyl-vinyl]-phenoxycarbonyl]-phenoxy]-ethoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-propoxycarbonyl-vinyl]-phenoxycarbonyl]-phenoxy]-ethoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-hexyloxycarbonyl-vinyl]-phenoxycarbonyl]-phenoxy]-ethoxycarbonyl]-1-methyl-ethylene];

poly [1-[6-[2-methoxy-4-[4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]- phenoxycarbonyl]-phenoxy]-ethoxycarbonyl]-1-methyl-ethylene];

poly [1-[6-[2-methoxy-4-[4-[(E)-2-methoxycarbonyl-vinyl]-phenoxycarbonyl]-phenoxy]-hexyloxycarbonyl]-1-methyl-ethylene-co-1-[2-[4-[4-[(E)-2-butyloxycarbonyl-vinyl]-phenoxycarbonyl]-phenoxy]-ethoxycarbonyl]-1-methyl-ethylene];

poly [1-[6-[2-methoxy-4-[3-fluoro-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene];

poly [1-[6-[2-methoxy-4-[4-[(E)-2-methoxycarbonyl-vinyl]-phenoxycarbonyl]-phenoxy]-hexyloxycarbonyl]-1-methyl-ethylene-co-1-[2-(4-((E)-2-methoxycarbonyl-vinyl]-phenoxy]-ethoxycarbonyl]-1-methyl-ethylene];

poly [1-[6-[4-[2-fluoro-4-[(E)-2-methoxycarbonyl-vinyl]-phenoxycarbonyl]-phenoxy]-hexyloxycarbonyl]-1-methyl-ethylene-co-1-[6-[4-[4-[(E)-2-methoxycarbonyl-vinyl]-phenyl]-phenoxy]-hexyloxycarbonyl]-1-methyl-ethylene];

poly [1-[8-[4-[2-methoxy-4-[(E)-2-methoxycarbonyl-vinyl]-phenoxycarbonyl]-phenoxy]-octyloxycarbonyl]-1-methyl-ethylene-co-1-[3-[4-[4'-[(E)-2-methoxycarbonyl-vinyl]-biphenyl-4-yl]-cyclohexyl]-propoxycarbonyl]-1-methyl-ethylene];

poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[6-[2-[(E)-2-methoxy-carbonyl-vinyl]-naphthalen-6-yl]-hexyloxycarbonyl]-1-methyl-ethylene].

Upon reading the present specification, various alternative embodiments will become obvious to the skilled artisan. These variations are to be considered within the present scope and spirit of the present invention which should only be limited by the claims that follow and their equivalents.

What is claimed is:

1. A polymer, which comprises repeating units of the formula:

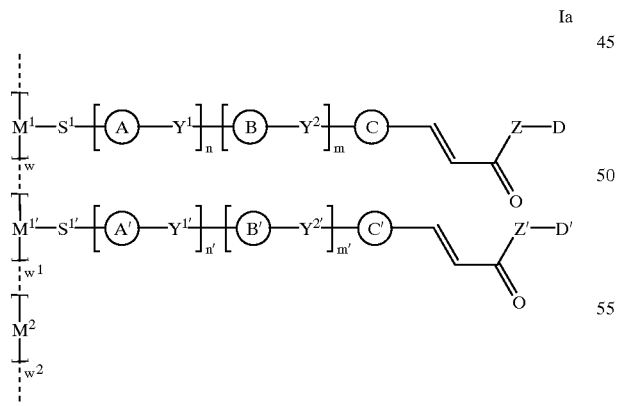

Ia wherein $M^1$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene derivative, comprising a vinylphenyl ether or vinylbenzyl ether and siloxane;

$S^1$ is a spacer unit;

ring A is unsubstituted phenylene, phenylene which is substituted with fluorine, chlorine, cyano, alkyl or alkoxy, pyridine-2-5-diyl, pyrimidine-2,5-diyl, 1,3-dioxane-2,5-diyl, cyclohexane-1,4-diyl, piperidine-1,4-diyl, or piperazine-1,4-diyl;

ring B is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl;

$Y^1$, $Y^2$ each independently is a single covalent bond, $-(CH_2)_t-$, $-O-$, $-CO-$, $-CO-O-$, $-O-OC-$, $-NR^4-$, $-CO-NR^4-$, $-R^4N-CO-$, $-(CH_2)_u-O-$, $-O-(CH_2)_u-$, $-(CH_2)_u-NR^4-$, or $-NR^4-(CH_2)_u-$, in which $R^4$ is hydrogen or lower alkyl;

t is a whole number from 1 to 4;

u is a whole number from 1 to 3;

m, n each independently is 0 or 1;

ring C is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthlene, or 2,6-naphthylene;

Z is $-O-$ or $-NR^5-$, in which $R^5$ is hydrogen or lower alkyl, or a second group of formula D, in which D is an unsubstituted $C_1-C_{20}$ straight chain alkyl group, an unsubstituted $C_1-C_{20}$ branched-chain alkyl group, a $C_1-C_{20}$ straight-chain alkyl group substituted with fluorine or chlorine, a branched-chain $C_1-C_{20}$ alkyl group substituted with fluorine or chlorine, an unsubstituted cycloalkyl residue with 3 to 8 ring atoms, or a cycloalkyl residue with 3 to 8 ring atoms substituted with fluorine, chlorine, alkyl or alkoxy;

$M^{1'}$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene derivative, and siloxane;

$S^{1'}$ is a spacer unit;

ring A' is unsubstituted phenylene, phenylene which is substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl, or piperazine-1,4-diyl;

ring B' is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl;

$Y^{1'}$, $Y^{2'}$ each independently is a single covalent bond, $-(CH_2)_t-$, $-O-$, $-CO-$, $-CO-O-$, $-O-OC-$, $-NR^4-$, $-CO-NR^4-$, $-R^4N-CO-$, $-(CH_2)_u-O-$, $-O-(CH_2)_u-$, $-(CH_2)_u-NR^4-$, or $-NR^4-(CH_2)_u-$, in which m', n' each independently is 0 or 1;

ring C' is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthlene, or 2,6-naphthylene;

Z' is —O— or —NR$^5$—, in which R$^5$ is hydrogen or lower alkyl, or a second group of formula D, in which D' is an unsubstituted $C_1$–$C_{20}$ straight-chain alkyl group, an unsubstituted $C_1$–$C_{20}$ branched-chain alkyl group, a $C_1$–$C_{20}$ straight-chain alkyl group substituted with fluorine or chlorine, a branched-chain $C_1$–$C_{20}$ alkyl group substituted with fluorine or chlorine, an unsubstituted cycloalkyl residue with 3 to 8 ring atoms or a cycloalkyl residue with 3 to 8 ring atoms substituted with fluorine, chlorine, alkyl or alkoxy, M$^2$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, straight-chain alkyl esters of acrylic acid, straight-chain alkyl esters of methacrylic acid, branch-chain alkyl esters of acrylic acid, branched-chain alkyl esters of methacrylic acid, alkyl esters of acrylic acid, allyl esters of methacrylic acid, alkyl vinyl ethers, alkyl vinyl esters, phenoxyalkyl acrylates, phenoxyalkyl methacrylates, phenylalkyl acrylates, phenylalkyl methacrylates, hydroxyalkyl acrylates with $C_1$–$C_{20}$ alkyl residues, hydroxyalkyl methacrylates with $C_1$–$C_{20}$ alkyl residues, acrylonitrile, methacrylonitrile, styrene, 4-methylstyrene, and siloxane;

w, w$^1$ and w$^2$ are molar fractions of the monomers with $0<w<1.0<w^1<1$ and $0<w^2\leq 0.5$.

2. The polymer according to claim 1, wherein ring A and A' is unsubstituted phenylene, phenylene which is substituted with fluorine, chlorine, cyano, alkyl or alkoxy, pyridine-2,5-diyl, pyrimidine-2,5-diyl, or cyclohexane-1,4-diyl;

ring B and B' is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, or cyclohexane-1,4-diyl;

Y$^1$, Y$^{1'}$, Y$^2$, Y$^{2'}$ each independently is a single covalent bond, —CH$_2$CH$_2$—, —O—, —CH$_2$—O—, —O—CH$_2$—, —CO—O—, or —O—OC—;

ring C and C' is unsubstituted phenylene, phenylene which is substituted with fluorine, chlorine, cyano, alkyl or alkoxy, pyrimidine-2,5-diyl, pyridine-2,5-diyl, 2,5-furanylene, 1,4-naphthylene, or 2,6-naphthylene;

Z and Z' is —O—; and

D and D' is straight-chain $C_1$–$C_{20}$ alkyl group, branched-chain $C_1$–$C_{20}$ alkyl group, a cycloalkyl residue with 5 to 6 ring atoms, or a cycloalkyl residue with 5 to 6 ring atoms which is substituted with alkyl or alkoxy.

3. The polymer according to claim 2, wherein n and n' are 0.

4. A polymer, which comprises repeating units of the formula:

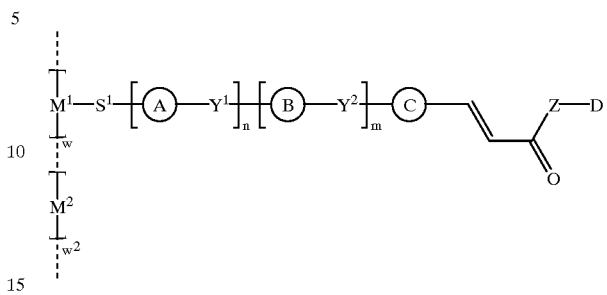

Ib wherein

M$^1$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene derivative, comprising a vinylphenyl ether or vinylbenzyl ether and siloxane;

S$^1$ is a spacer unit;

ring A is unsubstituted phenylene, phenylene which is substituted with fluorine, chlorine, cyano, alkyl or alkoxy, pyridine-2-5-diyl, pyrimidine-2,5-diyl, 1,3-dioxane-2,5-diyl, cyclohexane-1,4-diyl, piperidine-1,4-diyl, or piperazine-1,4-diyl;

ring B is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl;

Y$^1$, Y$^2$ each independently is a single covalent bond, —(CH$_2$)$_t$—, —O—, —CO—, —CO—O—, —O—OC—, —NR$^4$—, —CO—NR$^4$—, —R$^4$N—CO—, —(CH$_2$)$_u$—O—, —O—(CH$_2$)$_u$—, —(CH$_2$)$_u$—NR$^4$—, or —NR$^4$—(CH$_2$)$_u$—, in which R$^4$ is hydrogen or lower alkyl;

t is a whole number from 1 to 4;

u is a whole number from 1 to 3;

m, n each independently is 0 or 1;

ring C is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthlene, or 2,6-naphthylene;

Z is —O— or —NR$^5$—, in which R$^5$ is hydrogen or lower alkyl, or a second group of formula D, in which D is an unsubstituted $C_1$–$C_{20}$ straight chain alkyl group, an unsubstituted $C_1$–$C_{20}$ branched-chain alkyl group, a $C_1$–$C_{20}$ straight-chain alkyl group substituted with fluorine or chlorine, a branched-chain $C_1$–$C_{20}$ alkyl group substituted with fluorine or chlorine, an unsubstituted cycloalkyl residue with 3 to 8 ring atoms, or a cycloalkyl residue with 3 to 8 ring atoms substituted with fluorine, chlorine, alkyl or alkoxy;

M$^2$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, straight-chain alkyl esters of acrylic acid, straight-chain alkyl esters of methacrylic acid, branched-chain alkyl esters of acrylic acid, branched-chain alkyl esters of methacrylic acid, allyl esters of acrylic acid, allyl esters of methacrylic acid, alkyl vinyl ethers, alkyl vinyl esters, phenoxyalkyl acrylates, phenoxyalkyl methacrylates, phenylalkyl acrylates, phenylalkyl methacrylates, hydroxyalkyl acrylates with $C_1$–$C_{20}$ alkyl residues, hydroxyalkyl methacrylates with $C_1$–$C_{20}$ alkyl residues, acrylonitrile, methacrylonitrile, styrene, 4-methylstyrene, and siloxane;

w and $w^2$ are molar fractions of the monomers with $0<w<1$ and $0<w^2 \leq 0.5$.

5. The polymer according to claim 4, wherein ring A is unsubstituted phenylene, phenylene which is substituted with fluorine, chlorine, cyano, alkyl or alkoxy, pyridine-2,5-diyl, pyrimidine-2,5-diyl, or cyclohexane-1,4-diyl;

ring B is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, or cyclohexane-1,4-diyl;

$Y^1$, $Y^2$ each independently is a single covalent bond, —$CH_2CH_2$—, —O—, —$CH_2$—O—, —O—$CH_2$—, —CO—O—, or —O—OC—;

ring C is unsubstituted phenylene, phenylene which is substituted with fluorine, chlorine, cyano, alkyl or alkoxy, pyrimidine-2,6-diyl, pyridine-2,5-diyl, 2,5-furanylene, 1,4-naphthylene, or 2,6-naphthylene;

Z is —O—; and

D is a straight-chain $C_1$–$C_{20}$ alkyl group, branched-chain $C_1$–$C_{20}$ alkyl group, a cycloalkyl residue with 5 to 6 ring atoms, or a cycloalkyl residue with 5 to 6 ring atoms which is substituted with alkyl or alkoxy.

6. The polymer according to claim 5, wherein n is 0.

7. The polymer according to claim 6, wherein ring B is unsubstituted phenylene, phenylene which is substituted with fluorine, chlorine, cyano, alkyl or alkoxy, pyridine-2,5-diyl, pyrimidine-2,5-diyl, or cyclohexane-1,4-diyl;

$Y^2$ is a single covalent bond, —CO—O—, or —O—OC—;

m is 0 or 1;

n is 0;

ring C is unsubstituted phenylene, phenylene which is substituted with fluorine, chlorine, cyano, alkyl or alkoxy, 1,4-napthylene, or 2,6-naphthylene; and D is a straight chain $C_1$–$C_{12}$ alkyl group, or a branched-chain $C_1$–$C_{12}$ alkyl group.

8. A polymer, which comprises repeating units of the formula:

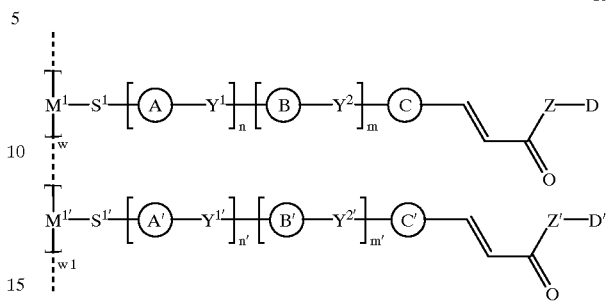

Ic wherein $M^1$ is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene derivative, comprising a vinylphenyl ether or vinylbenzyl ether and siloxane;

$S^1$ is a spacer unit;

ring A is unsubstituted phenylene, phenylene which is substituted with fluorine, chlorine, cyano, alkyl or alkoxy, pyridine-2-5-diyl, pyrimidine-2,5-diyl, 1,3-dioxane-2,5-diyl, cyclohexane-1,4-diyl, piperidine-1,4-diyl, or piperazine-1,4-diyl;

ring B is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl;

$Y^1$, $Y^2$ each independently is a single covalent bond, —$(CH_2)_t$—, —O—, —CO—, —CO—O—, —O—OC—, —$NR^4$—, —CO—$NR^4$—, —$R^4N$—CO—, —$(CH_2)_u$—O—, —O—$(CH_2)_u$—, —$(CH_2)_u$—$NR^4$—, or —$NR^4$—$(CH_2)_u$—, in which $R^4$ is hydrogen or lower alkyl;

t is a whole number from 1 to 4;

u is a whole number from 1 to 3;

m, n each independently is 0 or 1;

ring C is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthlene, or 2,6-naphthylene;

Z is —O— or —$NR^5$—, in which $R^5$ is hydrogen or lower alkyl, or a second group of formula D, in which D is an unsubstituted $C_1$–$C_{20}$ straight-chain alkyl group, an unsubstituted $C_1$–$C_{20}$ branched-chain alkyl group, a $C_1$–$C_{20}$ straight-chain alkyl group substituted with fluorine or chlorine, a branched-chain $C_1$–$C_{20}$ alkyl group substituted with fluorine or chlorine, an unsubstituted cycloalkyl residue with 3 to 8 ring atoms, or a cycloalkyl residue with 3 to 8 ring atoms substituted with fluorine, chlorine, alkyl or alkoxy;

$M^{1'}$ is a monomer unit selected from the group consisting of acrylate, methacrylate, 2-chloroacrylate, 2-phenylacrate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene derivative, and siloxane;

$S^{1'}$ is a spacer unit;

ring A' is unsubstituted phenylene, phenylene which is substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl, or piperazine-1,4-diyl;

ring B' is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl;

$Y^{1'}$, $Y^{2'}$, each independently is a single covalent bond, $-(CH_2)_t-$, $-O-$, $-CO-$, $-CO-O-$, $-O-OC-$, $-NR^4-$, $-CO-NR^4-$, $-R^4N-CO-$, $-(CH_2)_u-O-$, $-O-(CH_2)_u-$, $-O-(CH_2)_u-NR^4$, or $-NR^4-(CH_2)_u-$, in which m', n' each independently is 0 or 1;

ring C' is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthylene, or 2,6-napthylene;

Z' is $-O-$ or $-NR^5-$, in which $R^5$ is hydrogen or lower alkyl, or a second group of formula D, in which D' is an unsubstituted $C_1-C_{20}$ straight-chain alkyl group, an unsubstituted $C_1-C_{20}$ branched-chain alkyl group, a $C_1-C_{20}$ straight chain alkyl group substituted with fluorine or chlorine, a branched-chain $C_1-C_{20}$ alkyl group substituted with fluorine or chlorine, an unsubstituted cycloalkyl residue with 3 to 8 ring atoms, or a cycloalkyl residue with 3 to 8 ring atoms substituted with fluorine, chlorine, alkyl or alkoxy, w and $w^1$ are molar fractions of the monomers with $0<w<1$ and $0<w^1<1$.

9. The polymer according to claim 8, wherein ring A is unsubstituted phenylene, phenylene which is substituted with fluorine, chlorine, cyano, alkyl or alkoxy, pyridine-2,5-diyl, pyrimidine-2,5-diyl, or cyclohexane-1,4-diyl;

ring B is unsubstituted phenylene, phenylene which is substituted with fluorine, chlorine, cyano, alkyl or alkoxy, pyrimidine-2,5-diyl, pyrimidine-2,5-diyl, 1,4-naphthylene, 2,6-naphthylene, or cyclohexane-1,4-diyl;

$Y^1$, $Y^2$ each independently is a single covalent bond, $-CH_2CH_2-$, $-O-$, $-CH_2-O-$, $-O-CH_2-$, $-CO-O-$, or $-O-OC-$;

ring C is unsubstituted phenylene, phenylene which is substituted with fluorine, chlorine, cyano, alkyl or alkoxy, pyrimidine-2,5-diyl, pyridine-2,5-diyl, 2,5-furanylene, 1,4-naphthylene, or 2,6-naphthylene;

Z is $-O-$; and

D is a straight chain $C_1-C_{20}$ alkyl group, branched-chain $C_1-C_{20}$ alkyl group, a cycloalkyl residue with 5 to 6 ring atoms, or a cycloalkyl residue with 5 to 6 ring atoms which is substituted with alkyl or alkoxy.

10. The polymer according to claim 9, wherein n and n' are 0.

11. A polymer according to claim 1, which comprises poly [1-[2-[4-[(E)-2-methoxycarbonyl-vinyl]-phenoxy]-ethoxycarbonyl]-1-methyl-ethylene-co-1-[2-[4-[(E)-2-propoxycarbonyl-vinyl]-phenoxy]-ethoxycarbonyl]-1-methyl-ethylene-co-1-[2-hydroxy-ethoxycarbonyl]-1-methylethylene.

12. A polymer according to claim 4, which comprises poly [1-[6-[4-[4-[(E)-2-methoxycarbonyl-vinyl]-phenoxycarbonyl]-phenoxy]-hexyloxy-carbonyl]-1-methyl-ethylene-co-1-[2-ethylhexyloxycarbonyl]-1-methyl-ethylene].

13. A polymer according to claim 4, which comprises poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-ethoxycarbonyl-1-methyl-ethylene].

14. A polymer according to claim 4, which comprises poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-ethylhexyloxy-carbonyl-1-methyl-ethylene].

15. A polymer according to claim 8, which comprises poly [1-[6-[4-[2-methoxy-4-[(E)-2-methoxycarbonyl-vinyl]-phenoxycarbonyl]-phenoxy]-hexyloxycarbonyl]-1-methyl-ethylene-co-1-[2-[4-[2-methoxy-4-[(E)-2-methoxycarbonyl-vinyl]-phenoxycarbonyl]-phenoxy]-ethoxycarbonyl]-1-methyl-ethylene].

16. A polymer comprising poly [1-[3-[4-[4'-[(E)-2-methoxycarbonyl-vinyl]-biphenyl-4-yl]-cyclohexyl]-propoxycarbonyl]-1-methyl-ethylene].

17. A polymer comprising poly [1-[4-[(E)-2-methoxycarbonyl-vinyl]-phenoxycarbonyl]-1-methyl-ethylene].

18. A polymer comprising poly [1-[4-[(E)-2-methoxycarbonyl-vinyl]-phenylaminocarbonyl]-1-methyl-ethylene].

19. A polymer comprising poly [1-[2-[4-[(E)-2-methoxycarbonyl-vinyl]-phenoxy]-ethoxycarbonyl]-1-methyl-ethylene].

20. A polymer comprising poly [1-[6-[4-[4-[(E)-2-methoxycarbonyl-vinyl]-phenoxycarbonyl]-phenoxy]-hexyloxycarbonyl]-1-methyl-ethylene].

21. A polymer comprising poly [oxy-[4-[4-[4-[(E)-2-methoxycarbonyl-vinyl]-phenoxycarbonyl]-phenoxy]-butyl]-methyl-silylen].

22. A polymer comprising poly [1-[2-[(E)-2-methoxycarbonyl-vinyl]-naphthalin-6-yloxycarbonyl]-1-methyl-ethylene].

* * * * *

UNITED STATES PATENT AND TRADEMARK OFFICE
CERTIFICATE OF CORRECTION

PATENT NO.    : 6,335,409 B1
DATED         : January 1, 2002
INVENTOR(S)   : Herr et al.

It is certified that error appears in the above-identified patent and that said Letters Patent is hereby corrected as shown below:

<u>Column 41,</u>
Line 31, "alkyl" should read -- allyl --.

<u>Column 43,</u>
Line 39, "pyrimidine-2,6" should read -- pyrimidine-2,5 --.

<u>Column 46,</u>
Line 16, "methylethylene" should read -- methyl-ethylene --.

Signed and Sealed this

Sixteenth Day of July, 2002

*Attest:*

*Attesting Officer*

JAMES E. ROGAN
*Director of the United States Patent and Trademark Office*